United States Patent [19]
Lefkowitz et al.

[11] Patent Number: 6,096,705
[45] Date of Patent: Aug. 1, 2000

[54] INHIBITION OF AGONIST-SPECIFIC DESENSITIZATION OF β2 ADRENERGIC RECEPTORS

[75] Inventors: Robert J. Lefkowitz; Martin J. Lohse; Jeffrey L. Benovic; Marc G. Caron, all of Durham, N.C.

[73] Assignee: Duke University, Durham, N.C.

[21] Appl. No.: 08/038,072

[22] Filed: Mar. 29, 1993

Related U.S. Application Data

[63] Continuation of application No. 07/341,983, Apr. 24, 1989, abandoned.
[51] Int. Cl.[7] .................. A61K 38/16; A61K 31/715; C12N 9/12
[52] U.S. Cl. ..................... 514/2; 514/8; 514/13; 514/14; 514/56; 514/59
[58] Field of Search .................... 530/350, 402; 514/13, 2, 8, 14, 56, 59

[56] References Cited

PUBLICATIONS

The Journal of Biological Chemistry, vol. 262, No. 36, 17251–17253, Dec. 25, 1987.
Bulletin of the European Physiopathology of Respiration, vol. 21(5) G Cross, pp. 355–435.
The Journal of Biological Chemistry, vol. 264, 6707–6710, Apr. 25, 1989.
The Journal of Biological Chemistry, vol. 262, 6468–6471, May 15, 1987.
Proc. Natl. Acad. Sci. USA, vol. 83, 2797–2801, May 1986.
Nambi et al, "Desensitization of the turkey erythrocyte beta–adrenergic receptor n a cell–free system. Evidence that multiple protein kinases can phosphorylate and desensitize the receptor", The Journal of Biological Chemistry, vol. 260, No. 4, Feb. 24th 1985, pp. 2165–2171.
Vegesna et al, "Staurosporine inhibits protein kinase C and prevents phorbol ester–mediated leukotriene D4 receptor desensitization in RBL—1 cells", Molecular Pharmacology, vol. 33, No. 5, May 1988, pp. 537–542.
Hu et al, "Effects of protein kinase inhibitor 1–(5–isoquinolinylsulfonyl)–2–methylpipe razine, on beta–2 adrenergic receptor activation and desensitization in intact human lymphocytes", The Journal of Pharmacology and Experimental Therapeutics, vol. 249, No. 2, May 1989, pp. 492–498.
Lohse et al, "Inhyibition of beta–adrenergic receptor kinase prevents rapid homologous desensitization of beta 2–adrenergic receptors", Proceedings of the National Academy of Sciences of USA, vol. 86, No. 9, May 1989, pp. 2991–3442.
Hannun et al, Science, 243: 500–507 (1989).
Lefkowitz et al, J. Biol. Chem., 263 (aa):4993–4996 (1998).
Huganin et al, TIPS, 81:472–477 (1987).
Bulletin of the European Physiopathology of Respiration, vol. 21(5) G. Cross, pp. 355–435.
Hannun et al. *Science* 243: 500–507 (1989).
Lefkowitz et al *J. Biol Chem* 263(11):4993–4996 (1988).
Huganir et al. *TIPS* 81:472–477 (1987).
Blackshear et al. *FASEB J.* 2: 2957–2969 (1988).

*Primary Examiner*—David L. Fitzgerald
*Attorney, Agent, or Firm*—Nixon & Vanderhye P.C.

[57] ABSTRACT

The present invention relates to a method of inhibiting desensitization of a cell to the effects of a compound. The method comprises contacting the cell with an agent capable of inhibiting phosphorylation, by a protein kinase, of a receptor for the compound present on the surface of the cell. The present invention also relates to a method of screening a compound for its ability to inhibit desensitization. The method comprises:

i) contacting a receptor specific kinase-containing sample with the compound under conditions such that interaction between receptor specific kinase present in the sample and the compound can occur, and ii) determining the ability of the receptor specific kinase to phosphorylate the receptor for which it is specific.

8 Claims, 16 Drawing Sheets

INHIBITION OF AGONIST-SPECIFIC DESENSITIZATION OF β2 ADRENERGIC RECEPTORS

This is a continuation of application Ser. No. 07/341,983, filed on Apr. 24, 1989, now abandoned.

BACKGROUND OF THE INVENTION

1. Technical Field

The present invention relates, in general, to desensitization, and, in particular, to a method of inhibiting agonist-specific desensitization, to compounds suitable for use in such a method and to pharmaceutical compositions comprising same.

2. Background Information

Desensitization is a general phenomenon which is characterized by a reduced responsiveness following prolonged exposure to a hormone or drug. Occupancy of a wide variety of hormone and neurotransmitter receptors by agonists often leads to desensitization, that is, to a loss of receptor responsiveness to subsequent stimulation by agonist. This particular phenomenon is generally termed homologous desensitization. This is in contrast to the heterologous form of desensitization, which is defined as a loss of receptor responsiveness caused by agonist occupancy of other receptors.

Homologous desensitization has been most thoroughly studied for the β-adrenergic receptor (βAR)-adenylyl cyclase system (Benovic et al (1988) *Ann. Rev. Cell Biol.* 4:405–428). Homologous desensitization of βARs is accompanied by receptor phosphorylation (Sibley et al (1985) *J. Biol. Chem.* 260:3883–3886; Strasser et al (1986) *Biochemistry* 25:1371–1377). A cAMP-independent kinase, termed βAR kinase, has been described that specifically phosphorylates the agonist-occupied forms of the $\beta_2$-adrenergic receptor ($\beta_2$AR) and $\alpha_2$-adrenergic receptor (Benovic et al (1986) *Proc. Natl. Acad. Sci. USA* 83:2797–2801; Benovic et al (1987) *J. Biol. Chem.* 262:17251–17253) as well as light-activated rhodopsin (Benovic et al (1986) *Nature (London)* 322:867–872). Phosphorylation of the $\beta_2$AR by βAR kinase may trigger the process of functional uncoupling from the stimulatory guanine nucleotide binding protein, $G_s$ (Benovic et al (1987) *Proc. Natl. Acad. Sci. USA* 84:8879–8882).

While there have been several publications involving attempts at blocking desensitization (Mallorga et al (1980) *Proc. Natl. Acad. Sci. USA* 77:1341–1345; Shima et al (1983) *J. Biol. Chem.* 258:2083–2086; Heyworth et al (1984) *Biochem. J.* 222:189–194; Fano et al (1986) *J. Auton. Pharmacol.* 6:47–51; DeBernardi et al (1987) *Proc. Natl. Acad. Sci. USA* 84:2246–2250; and Toews (1987) *Mol. Pharmacol.* 32:737–742), none of these studies directly demonstrates the inhibition of agonist-specific desensitization. Moreover, none of the compounds utilized in these studies directly inhibit the βAR kinase. The identification of compounds which specifically inhibit this kinase could provide a method of inhibiting desensitization. The inhibition of desensitization should result in enhanced and prolonged receptor action in response to endogenous compounds and drugs. In the case of drugs, this means increased drug efficacy leading to the use of lower drug doses, and reduced side effects. In addition, it should allow prolonged treatment with drugs.

SUMMARY OF THE INVENTION

It is a general object of the invention to provide a method of blocking agonist-specific desensitization.

It is a specific object of the invention to provide compounds capable of inhibiting agonist-specific desensitization.

It is a further object of the invention to provide a pharmaceutical composition comprising as an active ingredient a compound capable of blocking agonist-specific desensitization.

It is another object of the invention to provide a method of augmenting the efficacy and duration of treatment of drugs, the continued administration of which results in desensitization.

It is a further object of the invention to provide a method of restoring the effectiveness of receptor-mediated responses to endogenous compounds such as hormones and neurotransmitters.

Further objects and advantages of the present invention will become clear to one skilled in the art from a reading of the description that follows.

In one embodiment, the present invention relates to a method of inhibiting desensitization of a cell to the effects of a compound. The method comprises contacting the cell with an agent capable of inhibiting phosphorylation, by a protein kinase, of a receptor for the compound present on the surface of the cell.

In another embodiment, the present invention relates to a method of screening a compound for its ability to inhibit desensitization. The method comprises:

i) contacting a receptor specific kinase-containing sample with the compound under conditions such that interaction between receptor specific kinase present in the sample and the compound can occur, and ii) determining the ability of the receptor specific kinase to phosphorylate the receptor for which it is specific.

In a further emobodiment, the present invention relates to an inhibitor of β adrenergic receptor kinase. The inhibitor consists essentially of a peptide corresponding to an intracellular domain of the $\beta_2$ adrenergic receptor.

In yet another embodiment, the present invention relates to a pharmaceutical composition. The composition comprises as an active ingredient the above-described peptide (or other agent) in an amount sufficient to exhibit an inhibitory effect on β adrenergic receptor kinase, together with a pharmaceutically acceptable carrier.

BRIEF DESCRIPTION OF THE DRAWINGS

FIG. 2A, rhodopsin was varied in the assay from 3 to 20 μM. The heparin concentrations were 0 (○), 0.21 (●), 0.42 (Δ), and 0.63 (▲) μM. FIG. 2B. ATP was varied in the assay from 33 to 100 μM. The heparin concentrations were 0 (○), 0.10 (●), 0.21 (Δ), and 0.31 (▲) μM.

FIG. 7A: Purified reconstituted $\beta_2$ARs were phosphorylated by purified βAR kinase with [γ-$^{32}$P]ATP in the presence of various concentrations of heparin. Curve-fitting gave an $IC_{50}$ value of 6.1±2.0 nM. 7C Relevant section of a representative autoradiogram. Data are means +SEM of three independent experiments. FIG. 7B: Permeabilized A431 cells were desensitized by incubation with 1 μM (−)-isoproterenol for 10 min at 37° C. in the presence of various concentrations of heparin. Desensitization was measured as the percent loss of stimulation by 10 μM (−)-isoproterenol of adenylyl cyclase activity in membranes. Curve-fitting gave an $IC_{50}$ value of 21±4 nM. Data are means±SEM of four independent experiments.

FIG. 8A: Autoradiogram obtained after a 10-day exposure at −70° C. FIG. 8B: Transverse densitometric scan of the autoradiogram. FIG. 8C: An aliquot of purified receptors from cells incubated without (−)-isoproterenol or heparin was photoaffinity-labeled with $^{125}$I-cyanopindolol diazirine in the absence (CON) or presence (ALP) of 10 μM alprenolol, followed by electrophoresis on the same gel (60 fmol per lane) and autoradiography. Similar results were obtained in two other experiments.

DETAILED DESCRIPTION OF THE INVENTION

Figure 1:
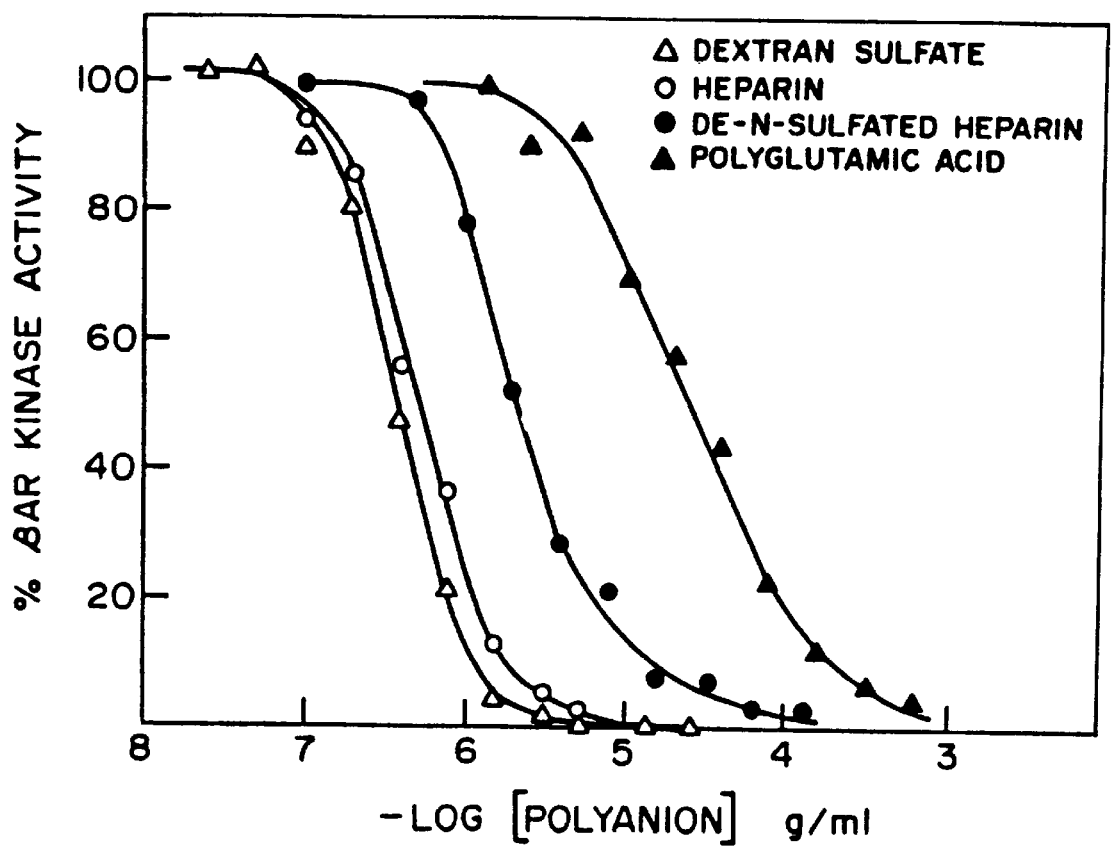
FIG. 1. Inhibition of βAR kinase by polyanions. Urea-treated rod outer segments were phosphorylated by βAR kinase in the presence of the indicated concentrations of polyanion. 100% activity corresponds to 11 pmol of phosphate incorporated during a 15-min incubation without inhibitor. Δ, dextran sulfate; ○, heparin; ●, de-N-sulfated heparin; ▲, polyglutamic acid.

The present invention relates to a method of inhibiting the desensitization of a cell to the effects of a compound (i.e. hormone or drug), the desensitization resulting from the continued contact of the cell with the compound. The method is based on the discovery that the loss of responsiveness of a cell to a particular compound is due to phosphorylation of the cell surface receptor for that compound.

In a specific embodiment, the present invention relates to a method of blocking the agonist specific (homologous) desensitization of a cell (tissue or organism) that results from prolonged exposure to the agonist. The method comprises contacting the cell (tissue or organism) subject to desensitization with a compound capable of inhibiting phosphorylation of the receptor for a particular agonist.

Compounds suitable for use in the present invention include those capable of inhibiting receptor kinases, for example, specific protein kinases involved in mediating homologous desensitization of adenylyl cyclase-coupled receptors (i.e. βAR kinase). (See also Blackshear (1988) *FASEB J.* 2:2957; Middleton (1988) *Ann. Allergy* 61:53; Hunnan (1988) *Science* 243:500.) Examples of such compounds include polyanions, advantageously, acid mucopolysaccharides such as heparin and dextran sulfate. Polycations, for example, polylysine, spermine and spermidine, are also capable of inhibiting the receptor specific kinase βAR kinase.

Highly receptor specific inhibition can be achieved using peptides corresponding to discrete domains of the receptor the phosphorylation of which is sought to be inhibited. For example, the $\beta_2AR$ peptides $\beta_2AR$ (219–243) (designated CIII-1 below), $\beta_2AR$ (56–74) (designated CI below), $\beta_2AR$ (57–71), $\beta_2AR$ (57–71; L→A, N→A), and βAR (57–71; K→A, R→A) are relatively potent inhibitors of βAR kinase, while $\beta_2AR$ (97–106) (designated EI below), $\beta_2AR$ (137–151) (designated CII below), $\beta_2AR$ (248–268) (designated CIII-2 below), $\beta_2AR$ (337–355) and $\beta_2AR$ (353–381) (designated CT-2 below) and $\beta_2AR$ (57–71, E→Q), which peptides also inhibit βAR kinase, are somewhat less effective. Methods of identifying receptor peptides capable of exerting an inhibitory effect on receptor kinases are set forth in the Examples that follow. The invention includes within its scope receptor peptides, for example, those set forth above.

The invention also relates to pharmaceutical compositions comprising as an active ingredient at least one inhibitor of at least one receptor kinase, together with a pharmaceutical carrier. Such compositions can include agents (for example, lipophilic reagents) that facilitate transport of the inhibitor across cell walls. The compositions can be in dosage unit for (i.e. pill, tablet or injectable solution, etc.). The amount of active ingredient to be included in such a composition, and the amount of active ingredient to be administered, can be determined by one skilled in the art without undue experimentation.

It will be appreciated that the method of the present invention can be used to restore the effectiveness of receptor mediated responses to endogenous compounds, such as hormones and neurotransmitters.

In another embodiment, the present invention relates to a method of screening compounds for their ability to block agonist-specific desensitization. The method can be practiced using a culture of cells permeabilized according to known protocols (for example, by treatment with digitonin), a cell lysate, or a cell free preparation of receptor kinase(s) (all of which will hereinafter be referred to as "receptor kinase containing sample"). The method comprises contacting the receptor kinase containing sample with a compound to be tested for its ability to inhibit desensitization under conditions such that interaction (i.e. binding) of the receptor kinase present in the sample and the compound can occur. The ability of the test compound to inhibit receptor kinase activity, and, therefore, block agonist-specific desensitization, is then determined by assaying for the ability of the kinase to phosphorylate the receptor for which it is specific. Assays for phosphorylation activity are known in the art and are exemplified below.

The following non-limiting Examples further describe the present invention.

EXAMPLE I

Inhibition of βAR Kinase by Polyanions

Heparin (average $M_r$=4000–6000), de-N-sulfated heparin, dextran sulfate (average $M_r$=5000), heparin sulfate, chondroitin sulfate B, chondroitin sulfate C, polyaspartic acid (average $M_r$=11,000), polyglutamic acid (average $M_r$=13,600), inositol hexasulfate, inositol hexaphosphate, pyridoxal phosphate, 2,3-diphosphoglycerate, glucosamine 2,6-disulfate, polylysine (average $M_r$=3300), spermine, and spermidine were purchased from Sigma. Frozen bovine retinas were from Hormel, while bovine cerebral cortex was obtained from a slaughterhouse.

βAR kinase was purified from bovine cerebral cortex by modification of procedure of Benovic et al (*J. Biol. Chem.* (1987) 262:9026–9032). Briefly, 250 g of bovine cerebral cortex were homogenized with a Brinkmann tissue disrupter and centrifuged (40,000× g, 30 min). The supernatant was then precipitated with 13–26% ammonium sulfate. This material was initially chromatographed on a Ultrogel AcA34 column equilibrated with 5 mM Tris-HCl, pH 7.5, 2 mM EDTA, 10 μg/ml leupeptin, 5 μg/ml pepstatin, 10 μg/ml benzamidine, 0.2 mM phenylmethylsulfonyl fluoride (buffer A). The peak activity was diluted with an equal volume of buffer A containing 0.04% Triton X-100 before being applied to a DEAE-Sephacel column. Elution was accomplished with a 0–80 mM NaCl gradient in buffer A containing 0.02% Triton X-100. The peak activity was then applied to a CM-Fractogel column and eluted with a 0–100 mM NaCl gradient in buffer A containing 0.02% Triton X-100. The purified kinase is stable at 4° C. for several months. For these studies the βAR kinase preparations were >75% pure.

Rod outer segments were prepared from bovine retinas by stepwise sucrose gradient centrifugation (Wilden et al *Biochemistry* (1982) 21:3014–3022). Rhodopsin kinase-free rod outer segments were prepared by treatment with 5 M urea (Shichi et al *J. Biol. Chem.* (1978) 253:7040–7046) and consisted of ~95% rhodopsin, as assessed by Coomassie Blue staining of sodium dodecyl sulfate-polyacrylamide gels.

Urea-treated rod outer segments were phosphorylated with βAR kinase as follows. Urea-treated rod outer segments (~4 μg of rhodopsin) were incubated with βAR kinase (~0.1 μg) for 10–15 min at 30° C. in the presence of 40 mM Tris-HCl, pH 7.4, 10 mM NaCl, 5 mM MgCl$_2$, 1.5 mM EDTA, and 65 μM ATP (~1 cpm/fmol) (total reaction volume was 40 μl). Reactions were stopped by the addition of 40 μl of sodium dodecyl sulfate sample buffer (see below) followed by sodium dodecyl sulfate-polyacrylamide gel electrophoresis. After autoradiography, the phosphorylated rhodopsin bands were excised and counted.

βAR kinase phosphorylates the $\beta_2AR$, the $\alpha_2$-adrenergic receptor, and rhodopsin in a stimulus-dependent fashion. Rhodopsin was utilized as the substrate in these experiments because of its ease of isolation. However, the inhibitory effects of polyanions observed with βAR kinase-catalyzed phosphorylation of rhodopsin have also been observed using reconstituted $\beta_2AR$ as the substrate.

Sodium dodecyl sulfate-polyacrylamide gel electrophoresis was performed by the method of Laemmli (*Nature* (1970) 227:680–685) using 10% homogeneous polyacrylamide slab gels. Sample buffer contained 8% sodium dodecyl sulfate, 10% glycerol, 5% 3-mercaptoethanol, 25 mM Tris-HCl, pH 6.5, and 0.003% bromphenol blue. After electrophoresis, gels were dried with a Bio-Rad gel dryer prior to autoradiography.

FIG. 1 demonstrates that a number of polyanions are potent inhibitors of βAR kinase-catalyzed phosphorylation of rhodopsin. In particular, heparin and dextran sulfate appear to be the most potent. De-N-sulfated heparin is ~8-fold weaker suggesting some importance of the N-sulfate. It is interesting to note that the inhibition by heparin, dextran sulfate, and de-N-sulfated heparin appears to involve a cooperative interaction of the polyanion with βAR kinase, as the data in FIG. 1 yield a Hill coefficient of ~2. Several other related acid mucopolysaccharides, such as heparan sulfate and chondroitin sulfates B and C, are significantly less potent than heparin (Table I). The $IC_{50}$ values of these compounds as well as those of a number of other anionic compounds are shown in Table I.

TABLE I

Effect of polyanions on the activity of βAR kinase
Phosphorylation of rhodopsin by βAR kinase in the presence of increasing concentrations of several polyanions was assessed as described above. The $IC_{50}$ is the concentration of compound which gave 50% inhibition and is presented as the mean ± S.E. with the number of determinations given in parenthesis. ND, molar concentration cannot be accurately determined.

| Compound | $IC_{50}$ μg/ml | μM |
|---|---|---|
| Heparan | 0.77 ± 0.10 (5) | 0.15 |
| De-N-sulfated heparin | 6.0 ± 2.4 (3) | ND |
| Heparan sulfate | 1.8 | ND |
| Chondroitin sulfate B | 25 | ND |
| Chondroitin sulfate C | 6 | ND |
| Dextran sulfate | 0.76 ± 0.21 (3) | 0.15 |
| Polyaspartic acid | 14 | 1.3 |
| Polyglutamic acid | 27 ± 2 (2) | 2.0 |
| Inositol hexasulfate | 12 ± 0.5 (2) | 13.5 |
| Inositol hexaphosphate | 3325 | 3600 |
| Pyridoxal phosphate | 222 | 900 |
| 2,3-Diphosphoglycerate | 838 | 1100 |
| Glucosamine 2,6-disulfate | 2800 | 7300 |

It is interesting that inositol hexasulfate is ~270 times more potent than inositol hexaphosphate. This suggests again that the sulfate moiety and not just the anionic character of the molecule is an important determinant in the inhibition of βAR kinase. Several other compounds such as pyridoxal phosphate, 2,3-diphosphoglycerate, and glucosamine 2,6-disulfate inhibited in the millimolar range. Similar results are observed when the βAR is used as the substrate with heparin again being the most potent inhibitor ($IC_{50}$~0.03 μM, data not shown).

Since heparin is the most potent inhibitor, the kinetics of heparin inhibition of βAR kinase were further characterized.

Figure 2A:
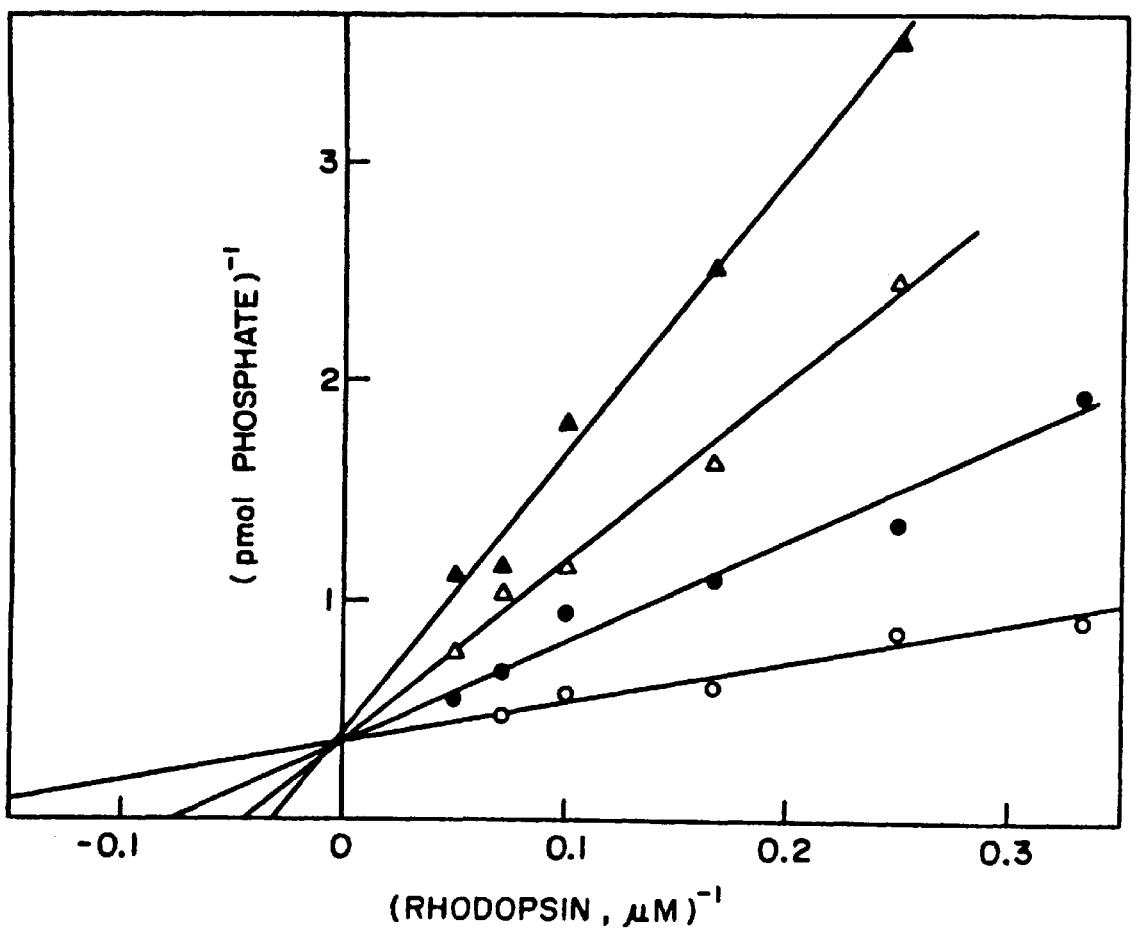
FIGS. 2A–2B (collectively, FIG. 2) Lineweaver-Burk plots for the inhibition of βAR kinase by heparin.
Figure 2B:
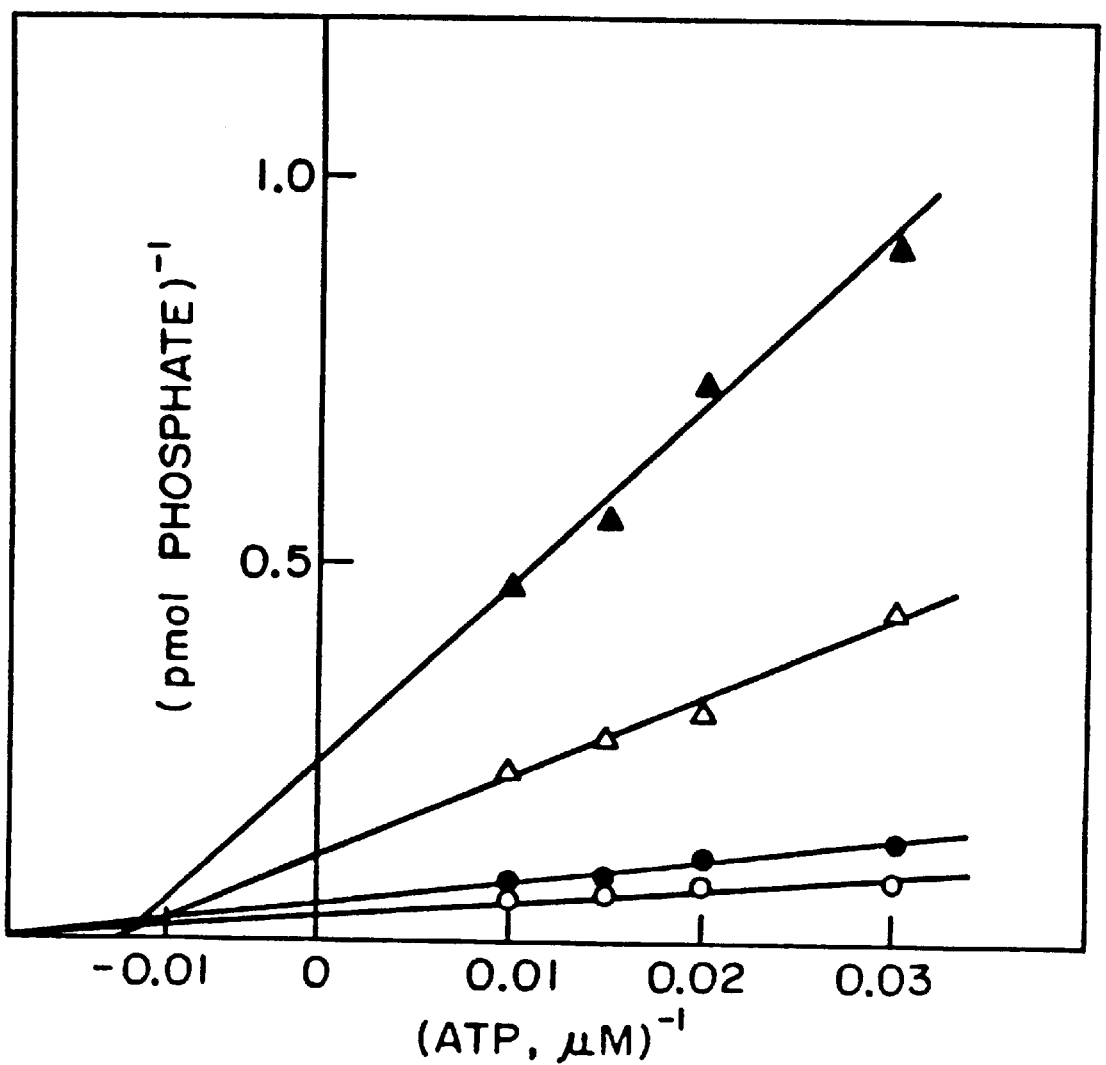

FIG. 2A shows a Lineweaver-Burk plot of data where the rhodopsin concentration is varied in the presence of several different concentrations of heparin. In the absence of heparin, a $K_m$=5.3 μM was obtained. Heparin appears to be a competitive inhibitor with respect to rhodopsin. A replot of these data (slope versus heparin concentration, not shown) yields a $K_i$~0.5 μg/ml (~0.10 μM). FIG. 2B shows a similar plot when the ATP concentration is varied in the presence of several different concentrations of heparin. These data suggest that heparin is a mixed type inhibitor with respect to ATP.

Figure 3:
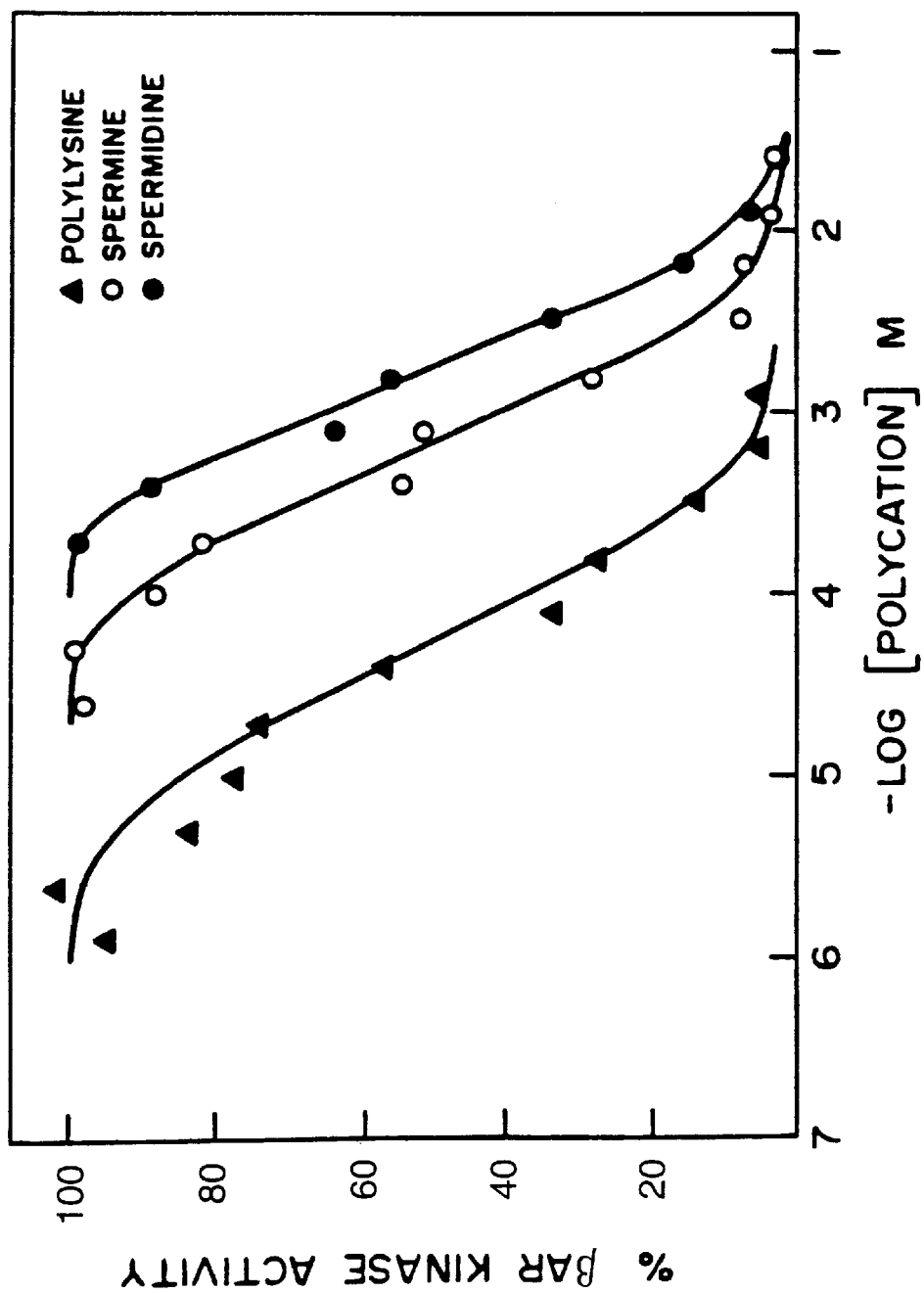
FIG. 3. Inhibition of βAR kinase by polycations. Urea-treated rod outer segments were phosphorylated by βAR kinase in the presence of the indicated concentrations of polycation. 100% activity corresponds to 13 pmol of phosphate incorporated during a 15-min incubation without inhibitor. ▲, polylysine; ○, spermine; ●, spermidine.

Polyanions are known to inhibit casein kinase II, whereas polycations, such as spermine, spermidine, and putrescine, are able to activate casein kinase II at low $Mg^{2+}$ or at 50–100 mM KCl concentrations (Hathaway et al (1982) *Curr. Top. Cell. Regul.* 21:101–127). In contrast, spermine and spermidine are weak inhibitors of βAR kinase (FIG. 3). Polylysine is more potent with an $IC_{50}$~69 μM. Similar results are observed at low $Mg^{2+}$ concentrations, as well as when 50 mM KCl is included in the incubation.

Figure 4:
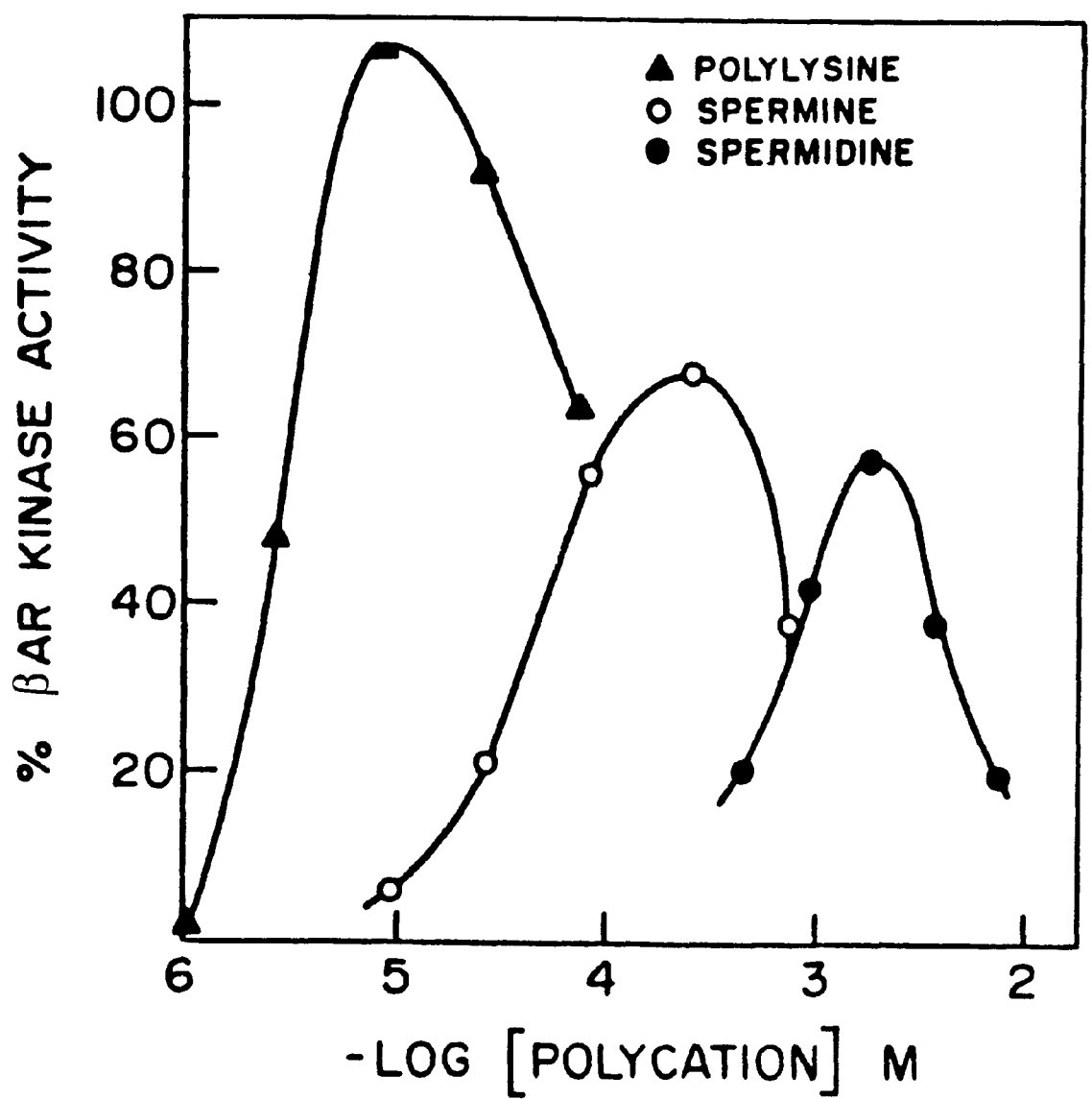
FIG. 4. Reversal of heparin inhibition by polycations. Urea-treated rod outer segments were phosphorylated by βAR kinase in the presence of 1.1 μM heparin and the indicated concentration of polycation. 100% activity represents phosphorylation in the absence of heparin and corresponds to 6 pmol of phosphate incorporated in a 15-min incubation. ▲, polylysine; ○, spermine; ●, spermidine.

At lower concentrations, polycations are able to partially reverse the inhibition of βAR kinase by heparin (FIG. 4). Polylysine is most effective with an $EC_{50}$~2.8 μM and a recovery of ~100% of the initial uninhibited activity. Spermine and spermidine also reverse the inhibition with $EC_{50}$ values of 40 and 630 μM and recoveries of ~68 and 57% activity, respectively. At higher concentrations these polycations are again inhibitory to the system. The mechanism of this reversal most likely represents a direct interaction of the polycation with heparin.

In summary, these results indicate that polyanions, in particular heparin and dextran sulfate, are potent inhibitors of the β-adrenergic receptor kinase. Polycations such as polylysine, spermine, and spermidine also inhibit βAR kinase activity. Polycations are also able to reverse the inhibitory effects of heparin.

EXAMPLE II

Inhibition of βAR Kinase Prevents Rapid Homologous Desensitization of $β_2$-ARs

[α-$^{32}$P]ATP, [γ-$^{32}$P]ATP, [$^3$H]cAMP, 125I-labeled cyanopindolol ($^{125}$I-cyanopindolol), and $^{125}$I-cyanopindolol diazirine were obtained from New England Nuclear; heparin (H-3125 from porcine mucosa), from Sigma. 1–5 (isoquinoline sulfonyl)-2-methylpiperazine (designated H-7), from Calbiochem; and digitonin, from Gallard Schlessinger. The peptide corresponding to residues 1–24 of the heat-stable inhibitor of cAMP-dependent protein kinase [PKI-(1–24) tetracosapeptide: Scott et al *Proc. Natl. Acad. Sci. USA* (1986) 83:1613–1616] and the $β_2$AR-(57–71) pentadecapeptide (Ala-Ile-Ala-Lys-Phe-Glu-Arg-Leu-Gln-Thr-Val-Thr-Asn-Tyr-Phe; Kobilka et al *Proc. Natl. Acad. Sci USA* (1987) 84:46–50) and $β_2$AR-(59–69) undecapeptide (Ala-Lys-Phe-Glu-Arg-Leu-Gln-Thr-Val-Thr-Asn) were chemically synthesized.

Purified $β_2$AR was phosphorylated by purified βAR kinase as follows. $β_2$ARs from hamster lung were purified by affinity chromatography and HPLC to >95% homogeneity (Benovic et al (1984) *Biochemistry* 23:4510–4518). βAR kinase was purified from bovine cerebral cortex by precipitation with ammonium sulfate, followed by chromatography on Ultrogel AcA34, DEAE-Sephacel, and CM-Fractogel to >75% purity as described (see Example I and Benovic et al (1987) *J. Biol. Chem.* 262:9026–9032). Purified $β_2$ARs were inserted into phosphatidylcholine vesicles by chromatography on Extracti-gel, followed by polyethylene glycol treatment and centrifugation at 280,000× g for 90 min (Cerione et al (1984) *Biochemistry* 23:4519–4525). Phosphorylation of the reconstituted receptors by purified βAR kinase was done in the presence of 50 μM (−)-isoproterenol as described (Benovic et al (1987) *J. Biol. Chem.* 262:9026–9032). Subsequently, the samples were subjected to sodium dodecyl sulfate polyacrylamide gel electrophoresis on 10% gels (Laemmli (1970) *Nature* 227:680–685). The phosphorylated $β_2$ARs were visualized by autoradiography, and the corresponding bands were cut out and their content of $^{32}$P quantified.

Permeabilization of cells was accomplished as follows. Human epidermoid carcinoma A431 cells were grown to about 95% confluence in Dulbecco's modified Eagle's medium supplemented with 10% fetal calf serum. Cells were harvested with collagenase, washed three times with calcium-free phosphate-buffered saline (PBS), then washed twice in 150 mM potassium glutamate/10 mM Hepes/5 mM EGTA/7 mM $MgCl_2$, pH 7.1 (KG buffer), and finally resuspended in KG buffer supplemented with 5 mM glucose and 2 mM ATP (KG-A buffer) at a density of 4×10$^7$ cells per ml.

The concentration of digitonin required to permeabilize the cells was found to vary considerably with cell density. At $4 \times 10^7$ cells per ml, about 0.015% digitonin was necessary to achieve permeabilization of >95% cells as assessed by staining with trypan blue. In all experiments, digitonin was added stepwise until >95% of the cells were trypan blue positive.

Desensitization of $\beta_2$ARs in A431 cells was effected as follows. Permeabilized cells in KG-A buffer (or, for controls, intact cells in PBS) were incubated with or without 1 $\mu$M (−)-isoproterenol for 10 min or the indicated times ($4 \times 10^7$ cells per ml). The incubation was terminated by addition of 10 vol of ice-cold KG buffer (or PBS, respectively), followed by centrifugation at 1000× g for 5 min. After three identical washes, cells were disrupted with a Polytron homogenizer in 5 mM Tris-HCl, pH 7.4/2 mM EDTA. Crude membranes were prepared by spinning the supernatant after low-speed centrifugation (1000× g for 5 min) at 40,000× g for 20 min.

Adenylyl cyclase activity in the membranes was determined as described by Salomon et al (*Anal. Biochem.* (1974) 58:541–548). The free $Mg^{2+}$ concentration in the assay was 4 mM. The incubation lasted for 20 min at 37° C.; accumulation of [$^{32}$P]cAMP was linear over this time period.

$\beta_2$ARs in permeabilized A431 cells were phosphorylated as follows. Permeabilized cells ($4 \times 10^8$) in 10 ml of KG-A buffer containing 1 mCi (1 Ci=37 GBq) of [$\gamma$-$^{32}$P]ATP were incubated with or without 1 $\mu$M (−)-isoproterenol (and other compounds as indicated) for 10 min at 37° C. All buffers used in these experiments contained 5 $\mu$g of soybean tryspin inhibitor, 5 $\mu$g of leupeptin, and 10 $\mu$g of benzamidine per ml and 0.1 mM phenylmethylsulfonyl fluoride. The reaction was terminated by addition of 30 ml of 150 mM potassium glutamate/5 mM EDTA/10 mM sodium phosphate, pH 7.1, at 0° C. and centrifugation at 1000× g for 5 min. After three identical washing steps, crude membranes were prepared as above. The membranes were solubilized with 2% digitonin, and 62 $_2$ARs were purified by affinity chromatography with alprenolol-Sepharose (Benovic et al (1984) *Biochemistry* 23:4510–4518). Equal amounts of $\beta_2$ARs from each sample (≈0.5 pmol, determined by radioligand binding using $^{125}$I-cyanopindolol) were subjected to sodium dodecyl sulfate polyacrylamide gel electrophoresis as described above. Gels were fixed in 40% (vol/vol) methanol and 15% (vol/vol) acetic acid and dried prior to autoradiography.

In addition, purified $\beta_2$ARs in these experiments were identified by photoaffinity labeling with 125I-cyanopindolol diazirine. Aliquots of the samples (≈60 fmol of $\beta_2$ARs) were desalted over Sephadex G-50 and incubated for 2 hr at 20° C. with 200 pM of the ligand with or without 10 $\mu$M alprenolol. Free ligand was removed by desalting as above, and the samples were irradiated with UV light for 3 min. The samples were loaded on the same gel as the samples described above.

Concentration-response curves were analyzed by nonlinear curve-fitting to the Hill equation as described (Lohse et al (1986) *Mol. Pharmacol.* 30:403–409). Adenylyl cyclase activity was expressed as the percentage of the activity in the presence of 10 mM NaF. Since NaF stimulates adenylyl cyclase via the stimulatory guanine nucleotide binding protein, $G_s$, this normalizes for effects that occur at the level of $G_s$ or the cyclase (i.e., which effects represent heterologous desensitization). Desensitization was assessed by measuring the loss of maximal stimulation by isoproterenol [determined with 10 $\mu$M (−)-isoproterenol] and was calculated as [1−stimulation (desensitized)/stimulation (control)]×100. For example, a decrease from 60% to 40% of NaF-stimulated activity corresponds to a desensitization of [1−(40/60)]×100=33%.

A variety of permeabilization techniques were tested for their ability to provide constant and reproducible access to the cytosol while leaving homologous desensitization unaltered. These included scrape-loading (McNeil et al (1984) *J. Cell Biol.* 98:1556–1564), electro-permeabilization (Knight et al (1986) *Biochem. J.* 234:497–506), and permeabilization with staphylococcal $\alpha$ toxin (Fussle et al (1981) *J. Cell Biol.* 91:83–94) and different detergents. Permeabilization with digitonin gave the most consistent results and was used for all future experiments.

Figure 5A:
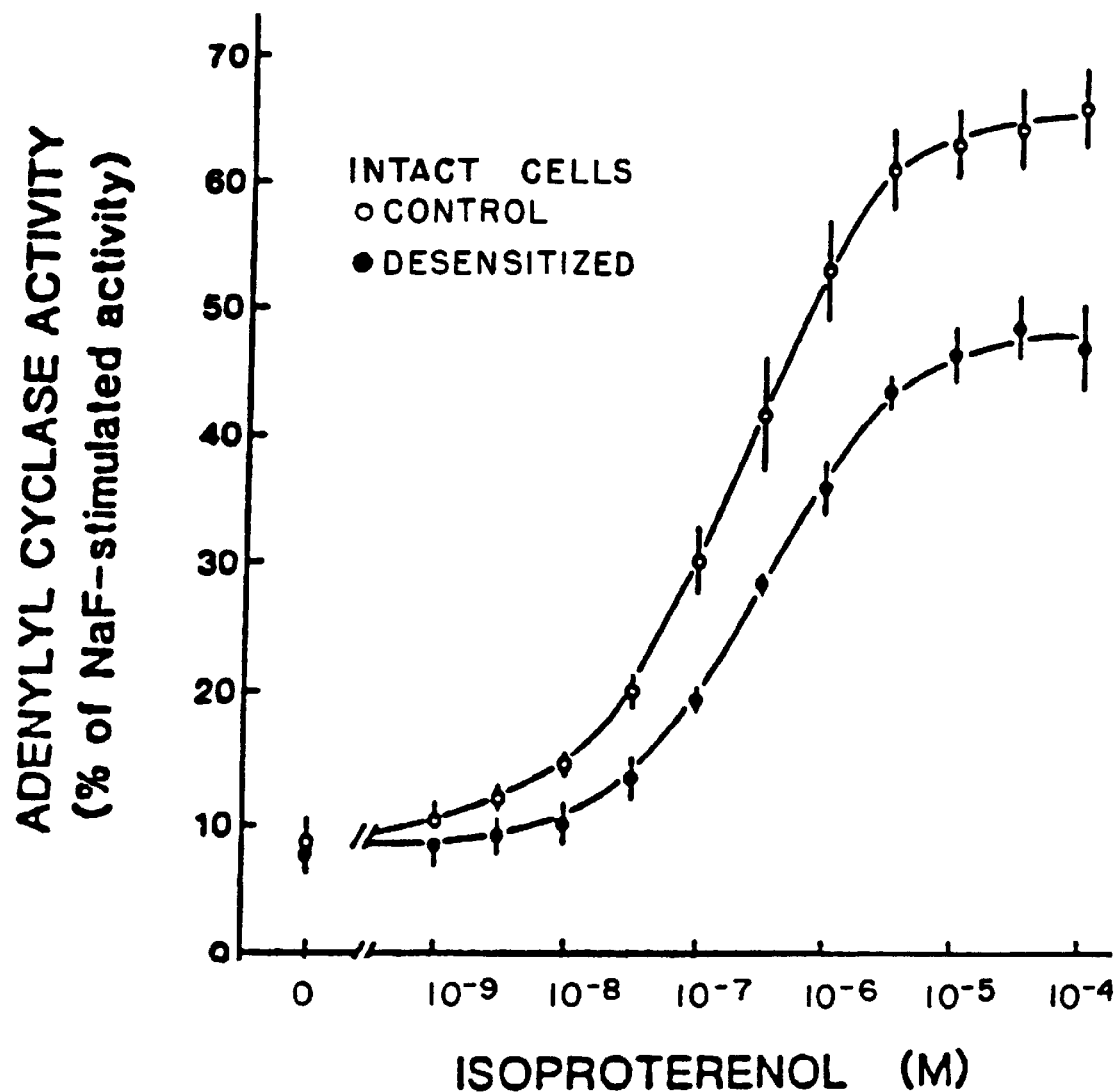
FIGS. 5A–5B (collectively, FIG. 5) Desensitization of $\beta_2$ARs in intact (FIG. 5A) and permeabilized (FIG. 5B) A431 cells. Cells were incubated for 10 min with (desensitized) (●) or without (control) (○) 1 μM (−)-isoproterenol as detailed. Adenylyl cyclase activities of membranes prepared from the cells were measured in the presence of various concentrations of (−)-isoproterenol and were expressed as percent of the activity in the presence of 10 mM NaF. Values for $EC_{50}$, maximal stimulation over basal ($E_{max}$, in percent of activity with 10 mM NaF), and activity in the presence of 10 mM NaF (=100%, in pmol of cAMP per mg of protein per min) were as follows: for control intact cells they were 200 n ($EC_{50}$), 56% ($E_{max}$), and 84±2 pmol/mg/min (100%); for desensitized intact cells they were 300 nM ($EC_{50}$), 40% ($E_{max}$), and 70±7 pmol/mg/min (100%) for control permeabilized cells they were 130 nM ($EC_{50}$), 62% ($E_{max}$), and 86±2 pmol/mg/min (100%) for desensitized permeabilized cells they were 190 nM ($EC_{50}$), 43% ($E_{max}$), and 69±3 pmol/mg/min (100%). Data are means±SEM of three independent experiments.
Figure 5B:
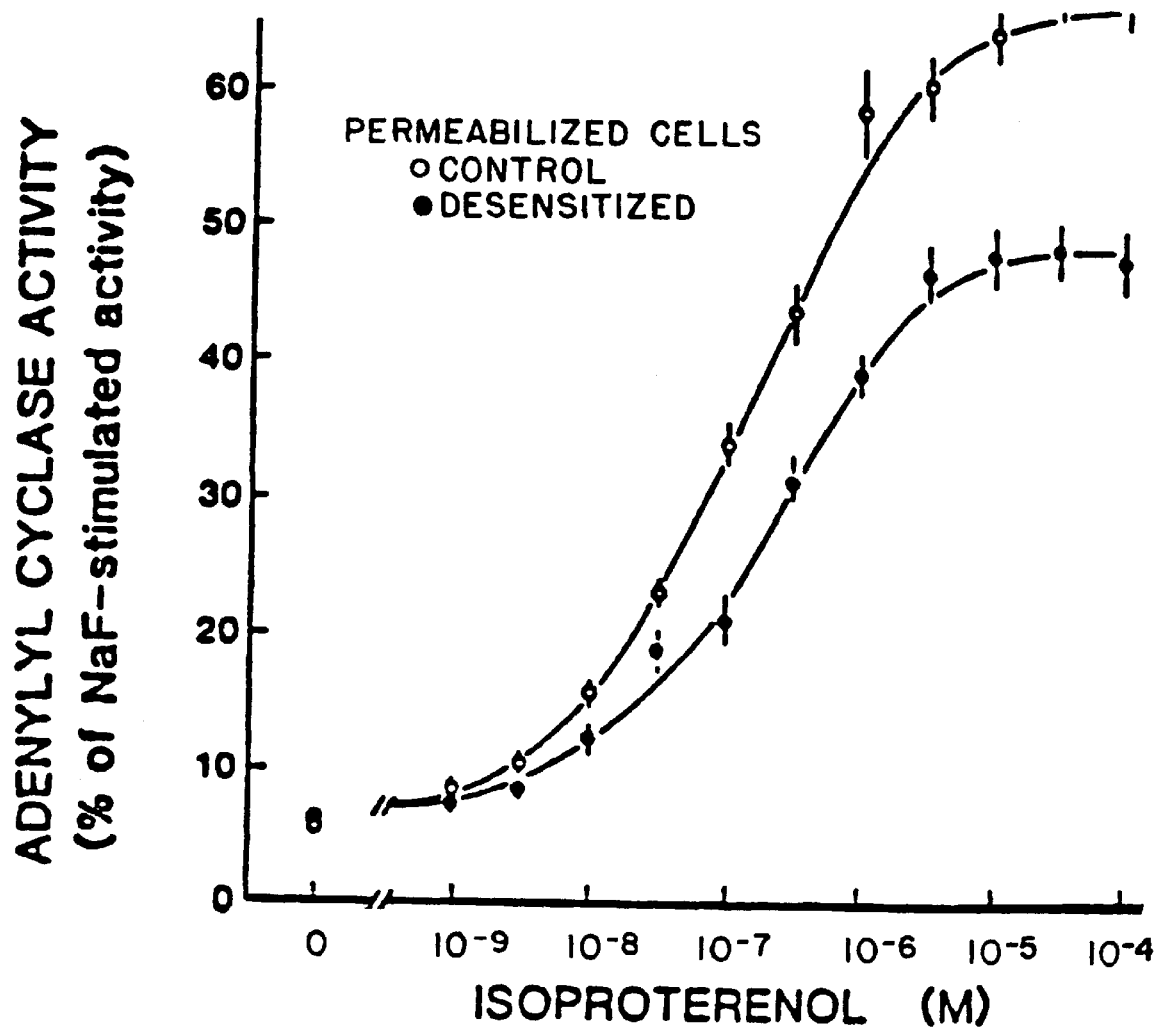

FIG. 5 shows that permeabilization of A431 cells with digitonin did not change the pattern of homologous desensitization to isoproterenol (1 $\mu$M). Isoproterenol-induced stimulation of adenylyl cyclase in membranes from cells incubated with 1 $\mu$M isoproterenol for 10 min at 37° C. was reduced in both potency and maximal effect as compared with membranes of control cells. In both intact and permeabilized cells, the extent of maximal stimulation over basal activity was reduced by the pretreatment from ≈60% to ≈40% of NaF-stimulated activity, corresponding to a desensitization of ≈30%.

Figure 6:
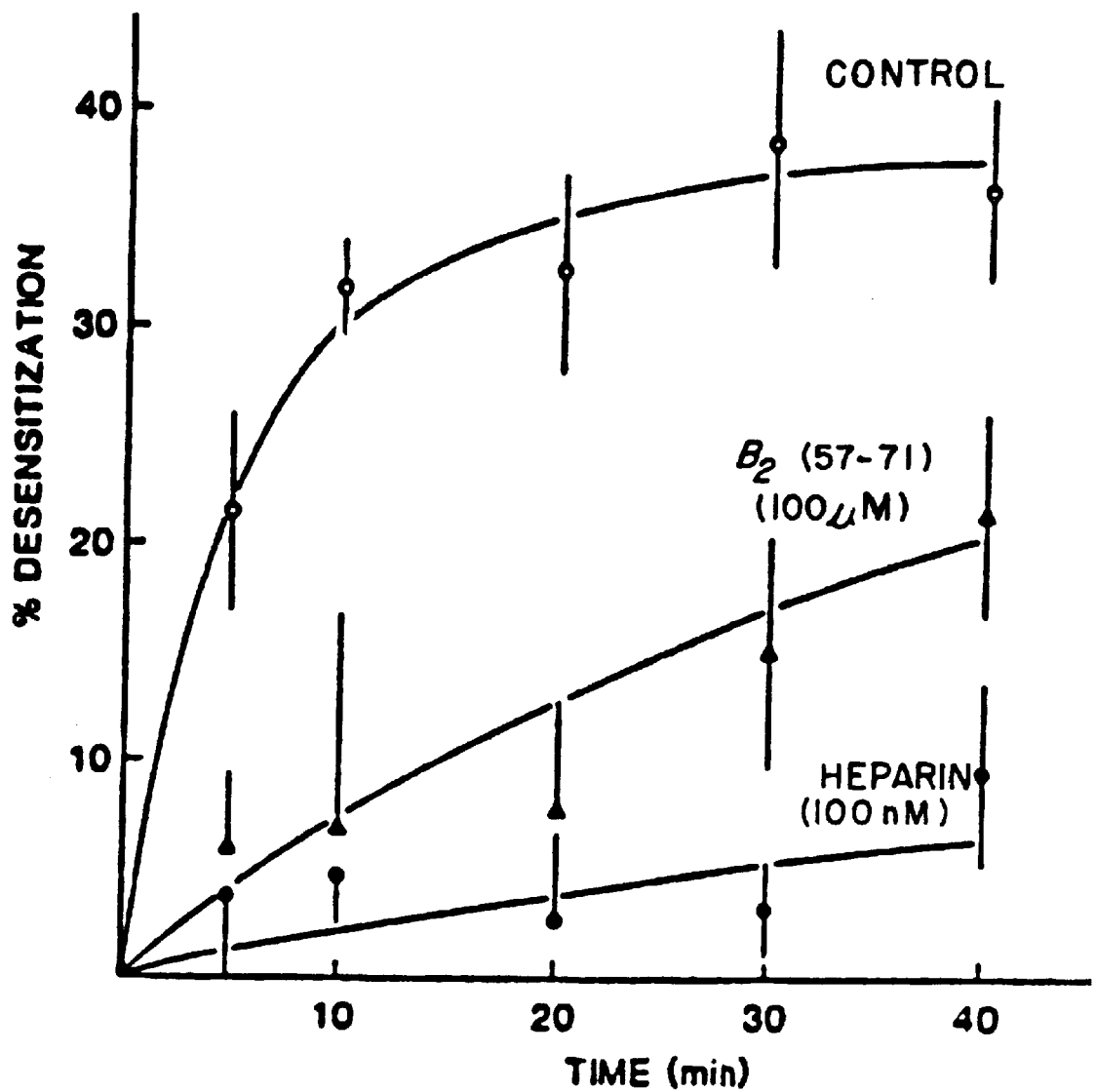
FIG. 6. Time course of $\beta_2$AR desensitization in permeabilized A431 cells. Permeabilized cells were incubated for the indicated periods of time with 1 μM (−)-isoproterenol alone (control) or in the presence of 100 μM of the peptide $\beta_2$AR-(57–71) [$\beta_2$(57–71)] or 100 nM heparin. Desensitization was measured as the percent loss of stimulation by 10 μM (−)-isoproterenol of adenylyl cyclase activity in membranes. Data are means±SEM of six (control) or three independent experiments.

FIG. 6 shows the time course of desensitization in permeabilized cells in the absence or presence of two inhibitors of $\beta$AR kinase, heparin (100 nM) and a peptide corresponding to the first intracellular loop of the human $\beta_2$AR [$\beta_2$AR-(57–71), 100 $\mu$M]. In the absence of inhibitors, desensitization occurred with a half-time of <5 min. $\beta_2$AR-(57–71) markedly slowed the rate of desensitization, and desensitization was almost completely abolished by 100 nM heparin. Neither compound affected desensitization in intact cells (data now shown).

It has been shown that heparin and its analogues may alter stimulation of adenylyl cyclase at micromolar concentrations (Amsterdam et al (1978) *Biochim. Biophys. Acta* 544:273–283). To ascertain that the inhibition of desensitization by heparin was not due to a reduced formation of cAMP, the accumulation of [$^{32}$P]cAMP from [$\alpha$-$^{32}$P]ATP added to permeabilized cells was determined. The presence of up to 1 $\mu$M heparin did not reduce [$^{32}$P] CAMP formation either in the presence or the absence of isoproterenol. Thus, the data indicate that compounds that inhibit $\beta$AR kinase slow down or suppress homologous desensitization.

Figure 7A:
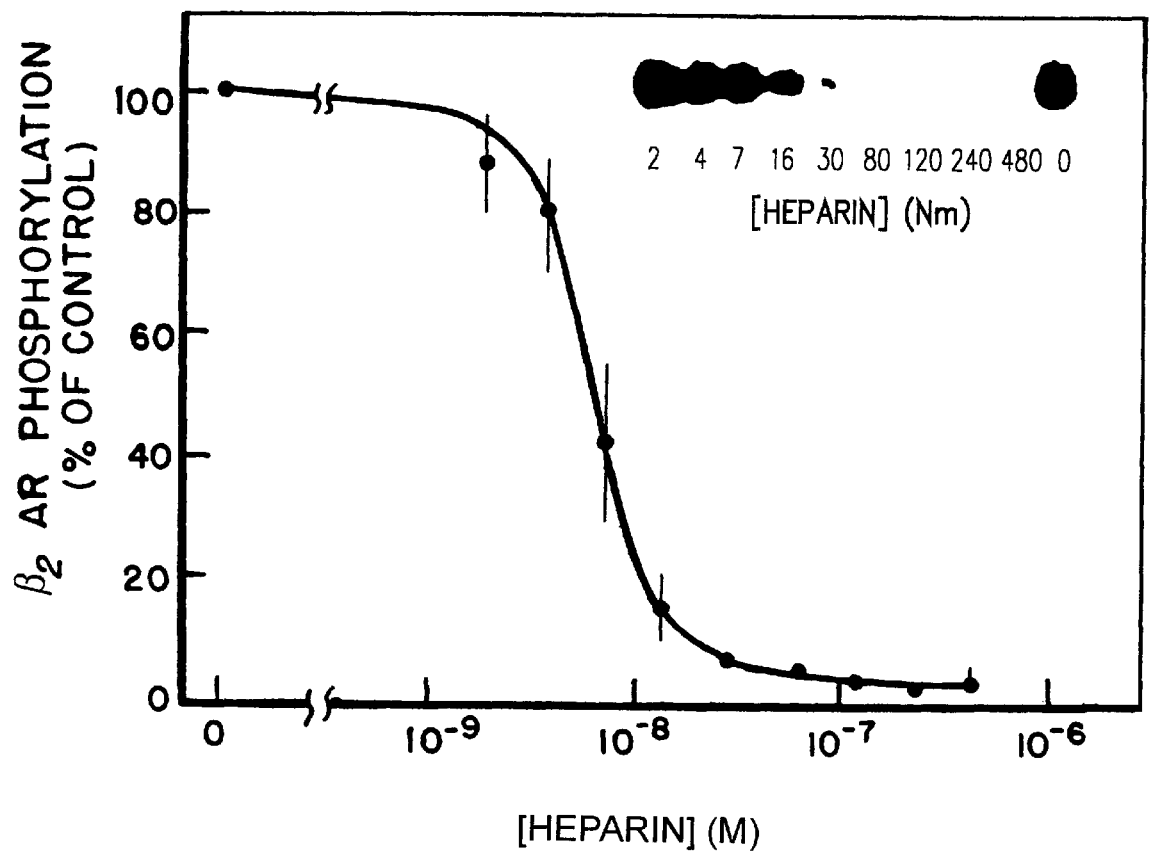
FIGS. 7A–7C (collectively, FIG. 7) Inhibition by heparin of $\beta_2$AR phosphorylation by βAR kinase in a reconstituted system (FIG. 7A) and of $\beta_2$AR desensitization in permeabilized A431 cells (FIG. 7B).
Figure 7B:
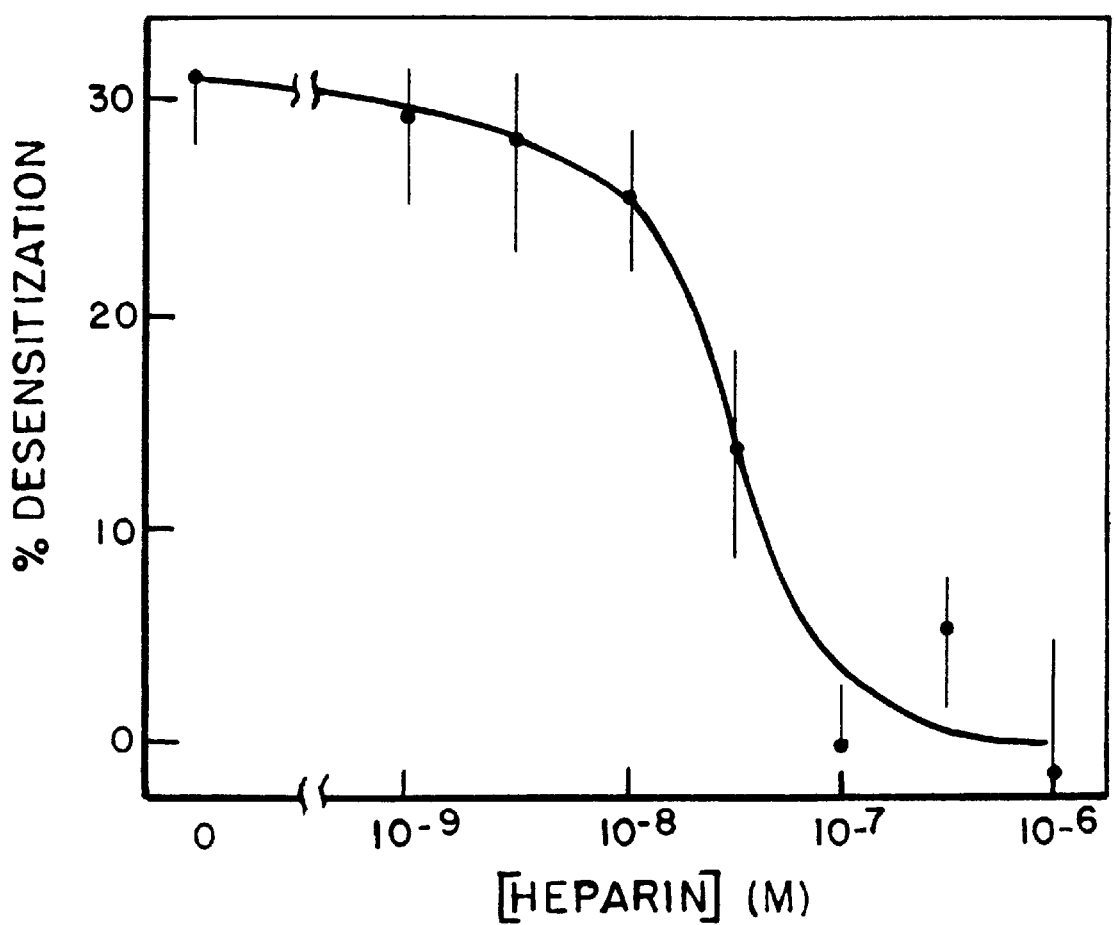
Figure 7C:
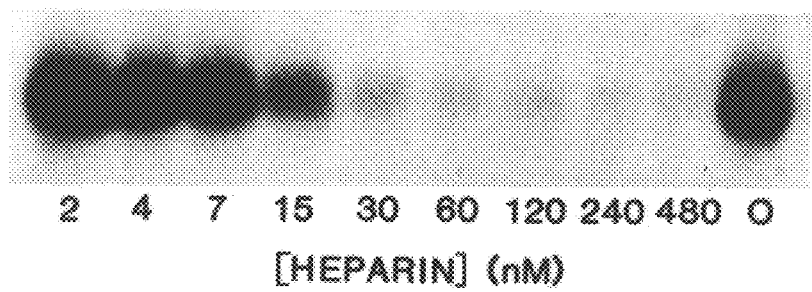

To show that these effects are indeed due to inhibition of $\beta$AR kinase, the concentration dependence for inhibition of $\beta$AR kinase activity in a reconstituted system was compared with that for inhibition of $\beta_2$AR desensitization by heparin (FIG. 7). Heparin inhibited phosphorylation of pure reconstituted $\beta_2$ARs by $\beta$AR kinase with an $IC_{50}$ value of 6 nM and caused almost complete inhibition at 30–100 nM (FIG. 7A). Desensitization of $\beta_2$ARs in permeabilized A431 cells was inhibited by heparin with an $IC_{50}$ value of 20 nM, and inhibition was virtually complete at concentrations above 100 nM. Thus, the concentration-response curves for the two effects are similar.

Figure 8A:
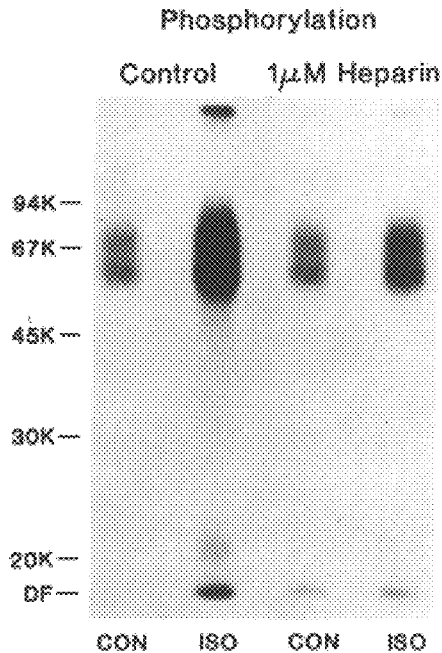
FIGS. 8A–8C (collectively, FIG. 8) Phosphorylation of $\beta_2$ARs in permeabilized A431 cells. Permeabilized cells were incubated with [γ-$^{32}$P]ATP without (CON) or with (ISO) 1 μM (−)-isoproterenol in the absence or presence of 1 μM heparin. $\beta_2$ARs were solubilized, purified by affinity chromatography, and electrophoresed on a 10% sodium dodecyl sulfate polyacrylamide gel, each lane containing 0.5 pmol of receptor.
Figure 8B:
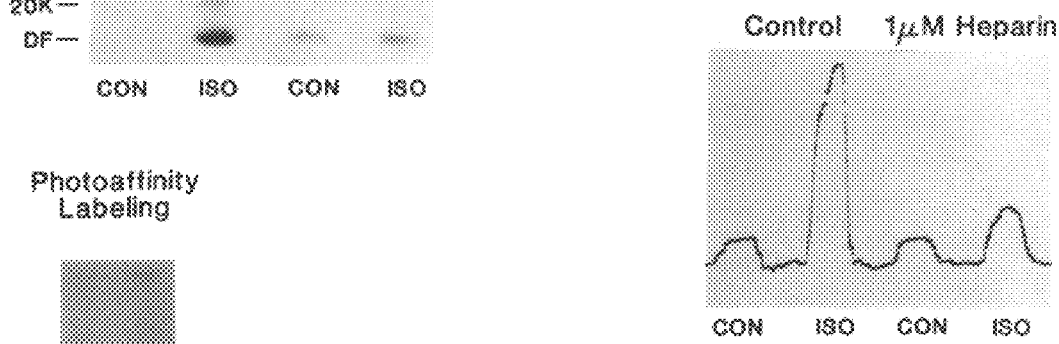
Figure 8C:
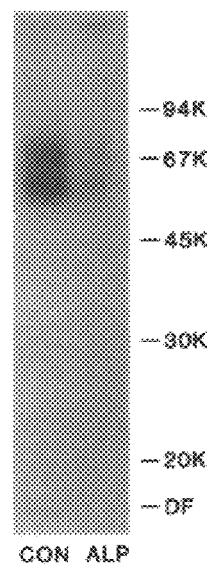

If the inhibition of desensitization by heparin is in fact caused by inhibition of $\beta$AR kinase, then it would be expected that heparin would reduce the isoproterenol-induced phosphorylation of $\beta_2$ARs in permeabilized cells. Therefore, permeabilized A431 cells were incubated with [$\gamma$-$^{32}$P]ATP with or without 1 $\mu$M isoproterenol in the absence or presence of 1 $\mu$M heparin. Incubation time (10 min) and conditions were the same as in the desensitization experiments reported in FIG. 7. In the absence of heparin, isoproterenol caused a 5-fold increase in the phosphorylation of the β$_2$ARs (FIG. 8). Heparin (1 μM) markedly reduced this increase while not affecting basal phosphorylation. Quantitation by scanning of the autoradiograms showed that heparin reduced the isoproterenol-induced phosphorylation by 50–80% in three experiments (FIG. 8B). Although some receptor degradation appeared to occur (as evidenced by a band of lower molecular weight), photoaffinity labeling with $^{125}$I-cyanopindolol diazirine confirmed that the purified phosphorylated bands represent β$_2$ARs (FIG. 8C). Thus, inhibition of β$_2$AR desensitization by heparin is paralleled by an inhibition of isoproterenol-induced receptor phosphorylation.

Finally, the effects of other kinase inhibitors and of analogues of the β$_2$AR peptide both on phosphorylation of reconstituted β$_2$ARs by βAR kinase and on desensitization in permeabilized A431 cells were compared (Table II). The peptide PKI-(1-24), which inhibits cAMP-dependent protein kinase with a K$_i$ value of 5×10$^{-9}$ M (Scott et al (1986) Proc. Natl. Acad. Sci. USA 83:1613–1615), had no effect at concentrations up to 1 μM on either βAR kinase activity or desensitization. H7, an inhibitor of protein kinase C and cyclic nucleotide-dependent protein kinases with K$_i$ values of about 5 μM (Hidaka et al (1984) Biochemistry 23:5036–5041), also did not affect either βAR kinase activity or desensitization at 1 μM and 10 μM. At 100 μM it caused ≈20% inhibition of both processes.

TABLE II

Inhibition of βAR kinase and of desensitization by kinase inhibitors and peptides of the β$_2$AR

| Compound | Concentration μM | Inhibition of βAR kinase, % | Inhibition of Desensitization, % |
|---|---|---|---|
| Kinase inhibitors | | | |
| Heparin | 0.1 | 96 ± 1 | 102 ± 16 |
| PKI-(1-24) | 1 | 0 ± 9 | 0 ± 12 |
| H7 | 1 | 3 ± 4 | 0 ± 4 |
|  | 10 | 2 ± 7 | 7 ± 5 |
|  | 100 | 19 ± 6 | 22 ± 14 |
| β$_2$AR peptides | | | |
| β$_2$AR-(57-71) | 100 | 80 ± 13 | 52 ± 12 |
| β$_2$AR-(59-69) | 100 | 0 ± 6 | 3 ± 12 |

Inhibition of βAR kinase and desensitization were measured as shown in FIG. 7. βAR kinase activity under control conditions corresponds to 6.5 ± 1.6 pmol of phosphate incorporated during a 30-min incubation. Desensitization under control conditions was 29 ± 4%. Data are means ± SEM of at least three experiments.

While the 15-amino acid peptide representing the first intracellular loop of the human β$_2$AR at a concentration of 100 μM caused significant inhibition of βAR kinase activity, the central 11-amino acid segment was virtually inactive in this respect. In parallel, the 15-amino acid peptide markedly inhibited desensitization (see also FIG. 6), whereas the shorter peptide did not affect it. These data confirm a correlation between inhibition of βAR kinase and inhibition of homologous desensitization.

EXAMPLE III

Synthetic Peptides of the Hamster β$_2$AR as Substrates and Inhibitors of the βAR Kinase Peptides were synthesized by tBOC chemistry on an Applied Biosystems 430A Synthesizer. Peptides were deblocked by HF treatment and were purified by reverse phase high performance liquid chromatography on a C18 column using a 0–50% acetonitrile gradient.

The β$_2$-adrenergic receptor from hamster lung was purified to apparent homogeneity by sequential affinity and high performance liquid chromatography as described (Benovic et al (1984) Biochemistry 23:4510–4518). The purified receptor was reinserted into phosphatidylcholine vesicles as previously described (Cerione et al (1983) Nature 306:562–566). The protein-lipid pellets were resuspended in 20 mM Tris-HCl, pH 7.2, 2 mM EDTA and used as a substrate for the βAR kinase.

βAR kinase was purified from bovine cerebral cortex by modification of a previously described procedure (Benovic et al (1987) J. Biol. Chem. 262:9026–9032). Briefly, 250 g of bovine cortex was homogenized and the resulting high speed supernatant fraction was precipitated with 13–26% ammonium sulfate. This material was initially chromatographed on an Ultrogel AcA34 column equilibrated with 5 mM Tris-HCl, pH 7.5, 2 mM EDTA, 5 μg/ml leupeptin, 5 μg/ml pepstatin, 15 μg/ml benzamidine, 0.2 mM phenylmethyl sulfonyl fluoride (buffer A). The peak activity was diluted 1:1 with buffer A containing 0.02% triton X-100 and applied to a DEAE Sephacel column. Elution was accomplished with a 0–80 mM NaCl gradient in buffer A containing triton X-100. The peak activity was then applied directly to a CM Fractogel column and eluted with a 0–100 mM NaCl gradient in buffer A containing triton X-100. The purified kinase was stored at 4° C.

Phosphorylation of βAR was accomplished by incubating reconstituted βAR (0.5–5 pmol/incubation) with βAR kinase (10–50 ng) in a buffer containing 20 mM Tris-HCl, pH 7.5, 2 mM EDTA, 10 mM NaCl, 5 mM MgCl2, 5 mM sodium phosphate, 0.5 mM ascorbic acid, 0.15 mM [γ-$^{32}$P] ATP (1–5 cpm/fmol) at 30° C. for the indicated time (see Figures indicated below and corresponding description). Some incubations also contained 50 μM (-)-isoproterenol. Incubations were stopped by the addition of 50 Al of SDS sample buffer followed by electrophoresis on 10% homogeneous polyacrylamide gels. Phosphorylated βAR was visualized by autoradiography and the corresponding bands were excised and counted to determine the pmol of phosphate incorporated.

Synthetic βAR peptides were phosphorylated as follows by βAR kinase. Synthetic peptides derived from the hamster lung β$_2$AR were incubated with βAR kinase (50–100 ng) in a buffer containing 50 mM Tris-HCl, pH 7.5, 2 mM EDTA, 10 mM NaCl, 5 mM MgCl$_2$, 1 mM dithiothreitol, 0.10 mM [(γ-32P]ATP (1–5 cpm/fmol) at 30° C. for the indicated time (see Figures indicated below and corresponding descriptions). The peptide concentrations varied from 0.5–6 mM. Peptides were separated from free ATP by one of several methods. In most experiments the reactions were stopped by the addition of 50 μl of SDS sample buffer or SDS urea sample buffer followed by electrophoresis on either a 15% homogeneous polyacrylamide gel or a 9% polyacrylamide gel containing 6.5 urea (see below). Following autoradiography the phosphorylated peptides were excised and counted to determine the amount of phosphate incorporated. In some experiments, samples were separated by reverse phase high performance liquid chromatography on a C18 column (Kuenzel et al (1985) Proc. Natl. Acad. Sci. USA 82:737–741). Following injection of the sample the column was washed with 30 ml of buffer (0.1 M sodium phosphate, pH 6.5, 0.1 M NaCl) before elution with a linear gradient from 0 to 50% acetonitrile. An alternative method involved direct application of the sample to phosphocellulose paper followed by extensive washing in 75 mM $H_3PO_4$ (Cook et al (1982) *Biochemistry* 21:5794). While this procedure gave comparable results for the CT-2 peptide, the CT-3 peptide did not appear to bind appreciably to the phosphocellulose paper.

The inhibition of substrate phosphorylation by βAR kinase in the presence of synthetic peptides was assayed as follows. Reconstituted βAR (0.2–1 pmol/incubation) was incubated with βAR kinase (10–30 ng) in a buffer containing 50 mM Tris-HCl, pH 7.5, 2 mM EDTA, 10 mM NaCl, 5 mM $MgCl_2$, 5 mM sodium phosphate, 50 μM (−)-isoproterenol, 0.10 mM [γ-$^{32}$P]ATP (1–3 cpm/fmol) at 30° C. for 30 min. Synthetic $β_2AR$ peptides were varied in concentration from 0 to 2 mM. Reactions were quenched by the addition of SDS sample buffer followed by gel electrophoresis. In some experiments urea treated rod outer segments (Wilden et al (1982) *Biochemistry* 21:3014–3022; Shichi et al (1978) *J. Biol. Chem.* 253:7040–7046) were used as the substrate for βAR kinase. To further define the specificity of the peptide inhibition, phosvitin, casein (see Example I) and the synthetic peptides CT-2 and CT-3 were used as substrates for βAR kinase.

SDS polyacrylamide gel electrophoresis was performed by the method of Laemmli (*Nature* (1970) 227:660–685) using 10 or 15% homogeneous slab gels. SDS sample buffer contained 8% SDS, 10% glycerol, 5% β-mercaptoethanol, 25 mM Tris-HCl, pH 6.5 and 0.003% bromphenol blue. SDS urea polyacrylamide gel electrophoresis was carried out using 6.5 M urea, 0.1% SDS, 100 mM $H_3PO_4$, pH 6.8 with Tris-HCl and 9% acrylamide (Swank et al (1971) *Anal. Biochem.* 39:462). SDS urea sample buffer contained 1% SDS, 8M urea, 10 mM $H_3PO_4$, pH 6.8 with Tris-HCl, 1% β-mercaptoethanol and 0.003% bromphenol blue.

Figure 9:
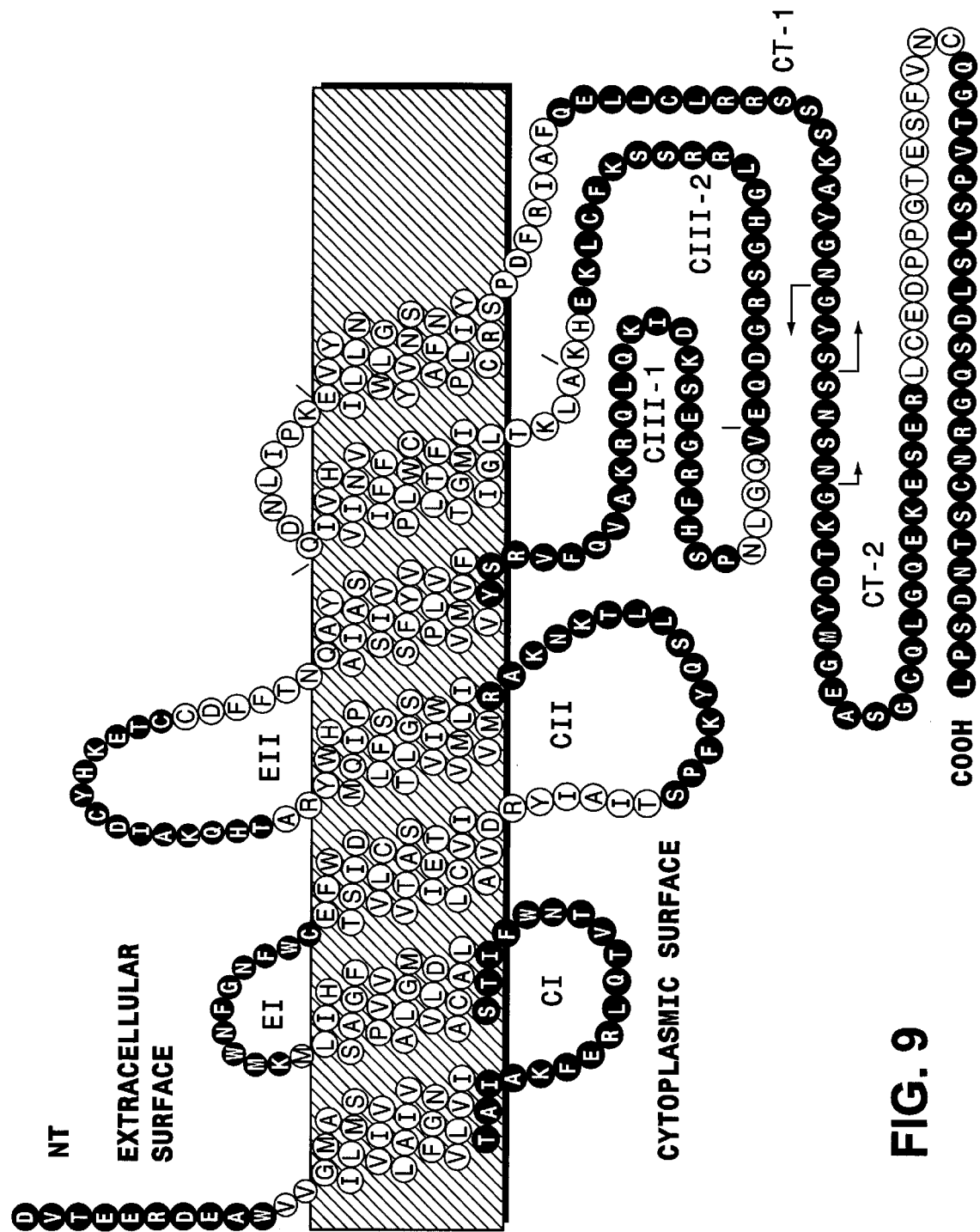
FIG. 9. Model for the organization of the hamster $\beta_2$AR in the plasma membrane. The amino acid sequence and proposed structure of the hamster $\beta_2$AR in the plasma membrane (Dixon et al (1986) Nature 321:75–79). The synthetic peptides used in this study are bracketed and labeled: NT—amino terminus; CI, CII, CIII—first, second and third intracellular loops; EI, EII—first and second extracellular loops; CT-1, CT-2, CT-3 —carboxyl terminus.

FIG. 9 presents the amino acid sequence and proposed topology of the hamster lung $β_2AR$. The synthetic peptides utilized in this study are highlighted and encompass the amino and carboxyl termini as well as the first and second extracellular and first, second and third intracellular loops.

Figure 10:
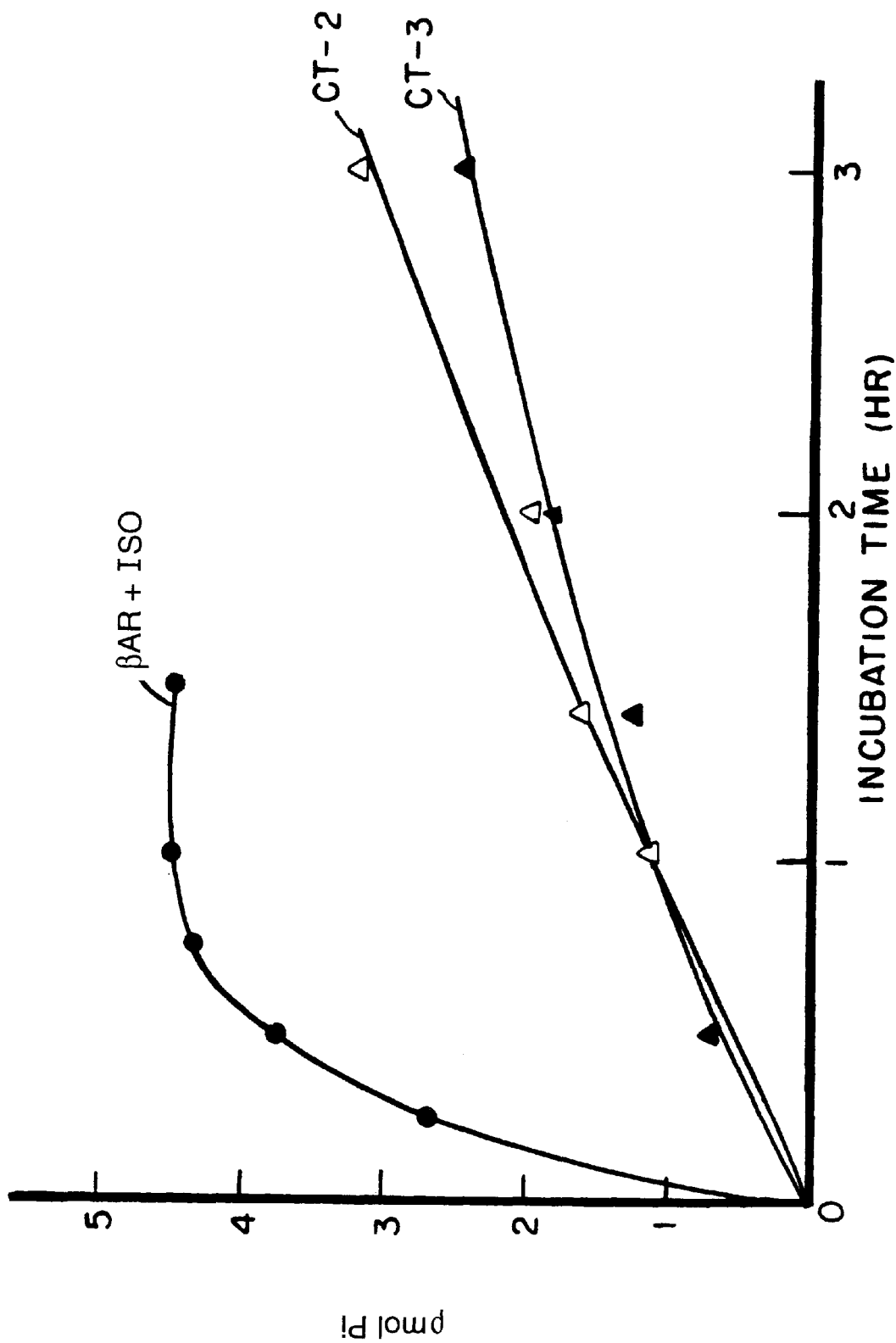
FIG. 10. Time course of phosphorylation of $\beta_2$AR and synthetic peptides by βAR kinase. Reconstituted hamster lung β2-adrenergic receptor (0.5 pmol) was phosphorylated by βAR kinase (~30 ng) in the presence (●) of 50 μM (−)-isoproterenol. Two synthetic carboxyl terminal peptides of the hamster lung $\beta_2$AR (CT-2 (Δ), CT-3 (▲)) were also phosphorylated by βAR kinase under identical conditions. Following the incubation period the reactions (20 μl) were stopped by addition of 50 μl of SDS sample buffer followed by electro-phoresis on a 10% ($\beta_2$AR) or 15% (CT-2, CT-3) homogeneous polyacrylamide gel.

Initial studies focused on determining whether any of these 10 peptides could serve as substrates for βAR kinase. The results shown in FIG. 10 demonstrate that two of the carboxyl terminal peptides (CT-2 and CT-3) are phosphorylated by βAR kinase. These peptides are, however, much poorer substrates than the agonist-occupied $β_2AR$ even when present at a 100,000-fold higher concentration. Phosphoamino acid analysis of the phosphorylated peptides reveals that CT-2 contains solely phosphoserine while CT-3 contains predominately phosphoserine with some phosphothreonine (data not shown). None of the other peptides tested are phosphorylated by βAR kinase, however, two of these peptides (CIII-2 and CT-1), which contain a consensus sequence for cAMP dependent protein kinase phosphorylation, serve as substrates for protein kinase A.

Figure 11:
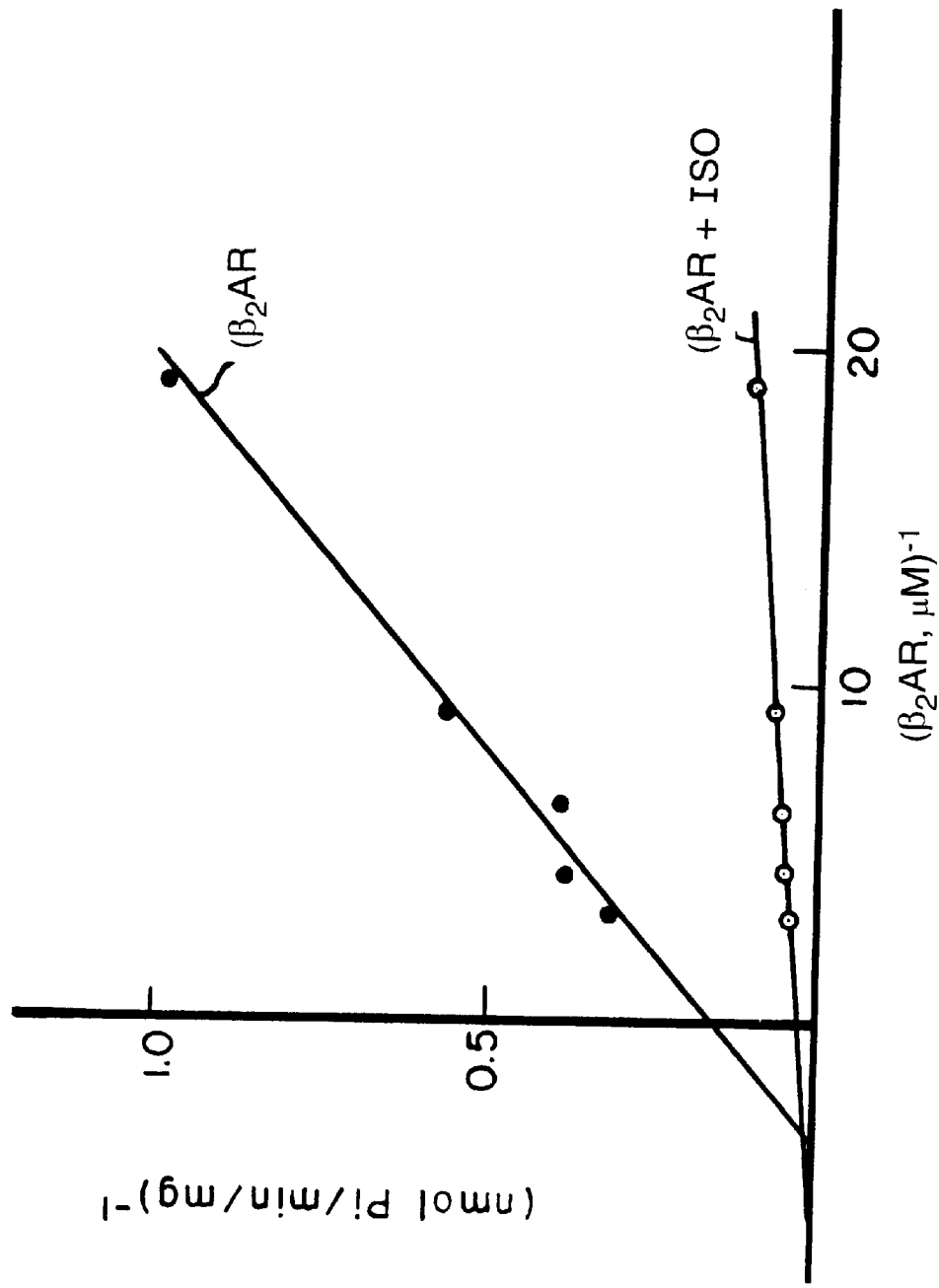
FIG. 11. Kinetic parameters of the βAR kinase for $\beta_2$AR. Reconstituted $\beta_2$AR (0.05–0.3 μM) was incubated for 15 min at 30° C. with purified βAR kinase (~30 ng) in the presence (○) or absence (●) of 50 μM (−)-isoproterenol. Reactions were stopped by the addition of SDS sample buffer before electrophoresis on a 10% SDS polyacrylamide gel. $^{32}$P-labeled receptor was determined by cutting and counting the dried gel following autoradiography.
Figure 12:
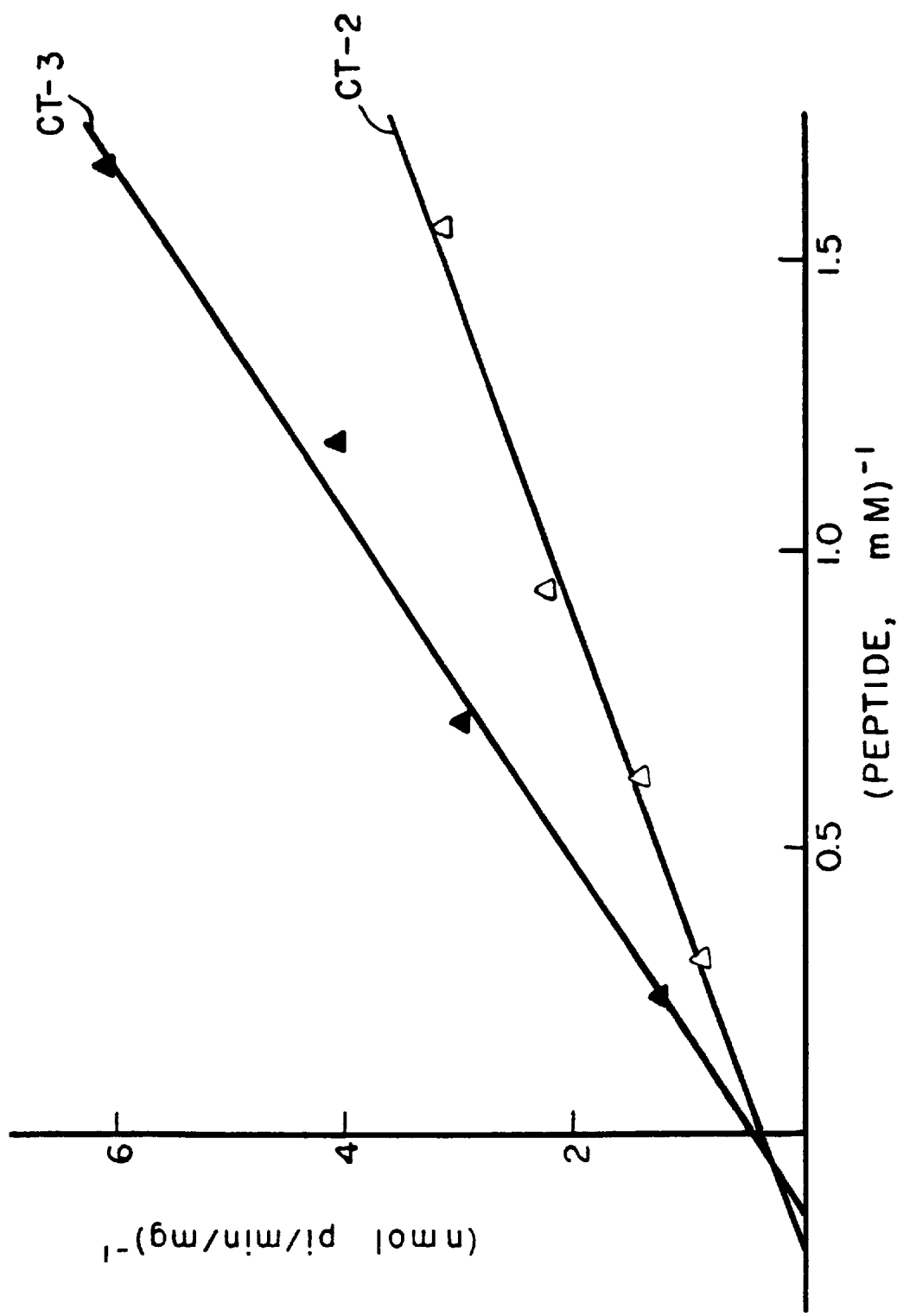
FIG. 12. Kinetic parameters of the βAR kinase for synthetic peptides CT-2 and CT-3. The synthetic $\beta_2$AR peptides CT-2 (0.6–3.3 mM; Δ) and CT-3 (0.6–4.3 mM; ▲) were incubated for 60 min at 30° C. with purified βAR kinase (~30 ng). Reactions were stopped by the addition of SDS urea sample buffer before electrophoresis on a 9% SDS urea polyacrylamide gel. $^{32}$P-labeled peptide was determined by cutting and counting the gel following autoradiography.

The kinetics of $β_2AR$ phosphorylation by βAR kinase in the presence or absence of the β-agonist isoproterenol are shown in FIG. 11. It is evident that the major agonist-promoted difference in the phosphorylation of the receptor is in the Vmax, with the agonist-occupied receptor having an ~6 fold higher Vmax (37 vs 6.6 nmol Pi/min/mg, Table III). In contrast, the Km of the receptor varies only 1.8-fold (0.16 vs 0.29 μM). Overall, the agonist-occupied receptor is an ~10-fold better substrate than the unoccupied receptor as assessed by the Vmax/Km ratio. In contrast, the phosphorylation of the synthetic BEAR peptides by βAR kinase have strikingly different kinetics (FIG. 12). The carboxyl peptide CT-2 is phosphorylated by βAR kinase with a Km ~5 mM and a Vmax ~2.8 nmol Pi/min/mg while CT-3 has a Km ~8 mM and a Vmax ~2.4. A comparison of the Vmax/Km ratios demonstrates that the agonist-occupied receptor is an ~$10^6$-fold better substrate than the carboxyl peptides (Table III). The major difference between the substrates (receptor vs. peptides) is in the Km obtained with a 32,000–50,000 fold difference.

TABLE III

βAR kinase phosphorylation of $β_2AR$ and synthetic $β_2AR$ peptides

| SUBSTRATE | Km (μM) | Vmax (nmol/min/mg) | Vmax/Km | Ratio |
|---|---|---|---|---|
| $β_2AR$ + ISO | 0.16 | 37 | 231 | 1 |
| $β_2AR$ | 0.29 | 6.6 | 23 | $10^{-1}$ |
| CT-2 | 5200 | 2.8 | $5.4 \times 10^{-4}$ | $2.3 \times 10^{-6}$ |
| CT-3 | 7900 | 2.4 | $3.0 \times 10^{-4}$ | $1.3 \times 10^{-6}$ |

Overall, these results demonstrate that the intact $β_2AR$ serves as a much better substrate for βAR kinase than the peptides suggesting that the secondary or tertiary structure of the receptor is important for kinase recognition. These results also indicate that βAR kinase recognizes other regions of the receptor in addition to the phosphorylation sites at the carboxyl terminus.

Figure 13:
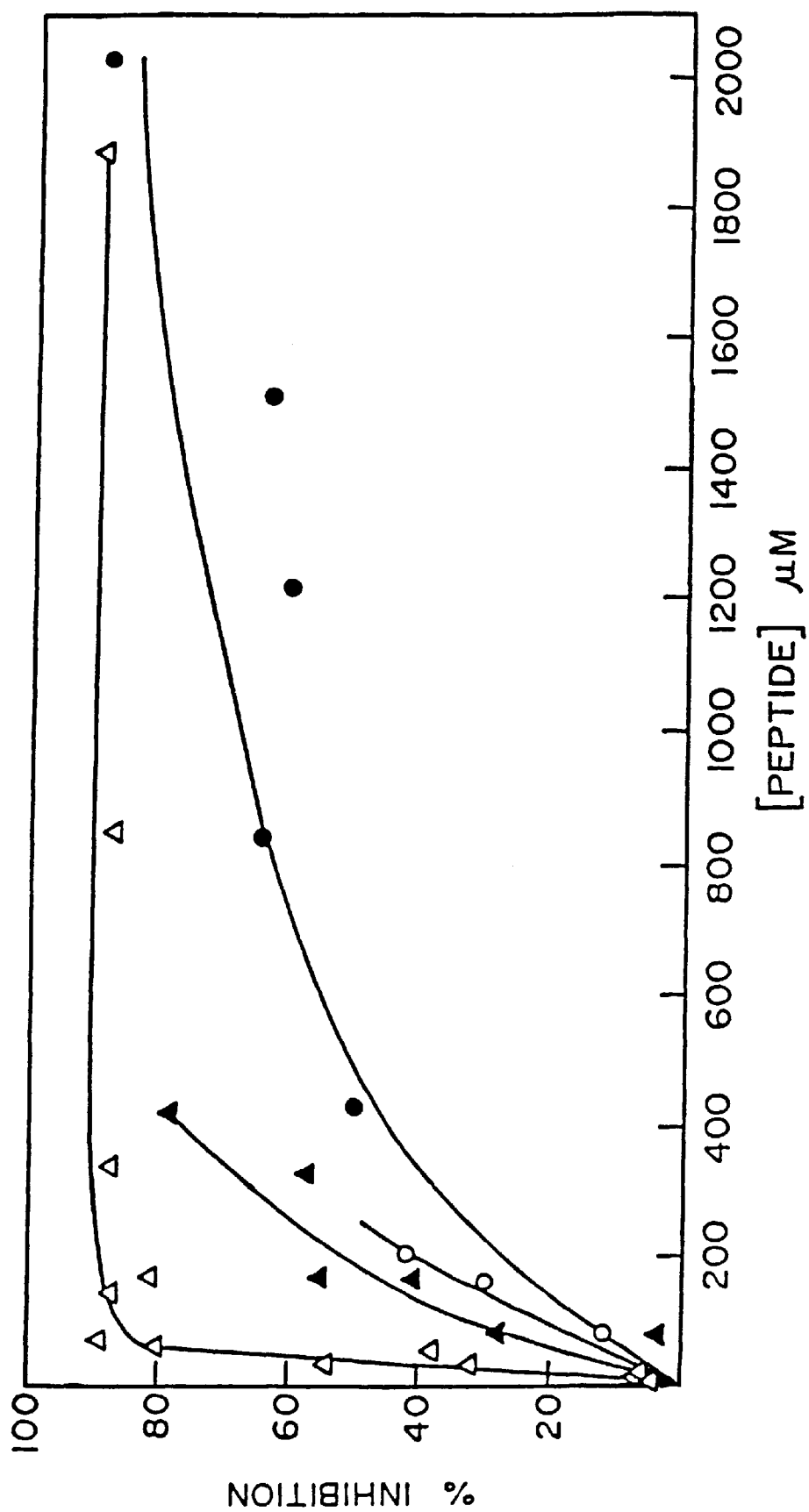
FIG. 13. Inhibition of $\beta_2$AR phosphorylation by synthetic peptides. Reconstituted $\beta_2$AR (~0.4 pmol) was incubated for 30 min at 30° with purified βAR kinase (~30 ng) in the presence of 50 mM Tris-HCl, pH 7.5, 2 mM EDTA, 10 mM NaCl, 5 mM MgCl$_2$, 5 mM sodium phosphate, 50 μM (−)-isoproterenol and 0.10 mM [γ$^{32}$P]ATP (2.0 cpm/fmol). Synthetic $\beta_2$AR peptides were varied from 0 to 1 mM and included CI (Δ), CII (▲), CIII-2 (○) and CT-1 (●). Reactions were stopped by the addition of SDS polyacrylamide gel. $^{32}$P-labeled receptor was determined by cutting and counting the dried gel following autoradiography.

To address whether other regions of the $β_2AR$ might interact with βAR kinase, the synthetic peptides were tested as potential inhibitors of $β_2AR$ phosphorylation. As shown in FIG. 13 a number of synthetic peptides are potent inhibitors of βAR phosphorylation by βAR kinase. These include the first intracellular loop (C-I) which has an $IC_{50}$ ~40 μM as well as the second and third intracellular loops (CII, CIII-1 and CIII-2) and the carboxyl terminus (CT-1 and CT-2) which have $IC_{50}$s ranging from 70–320 μM (Table IV). Several peptides do not inhibit the phosphorylation when tested at a concentration of ~0.5 mM (NT, E-II, and CT-3). These results indicate that βAR kinase may interact with multiple regions of the receptor, perhaps explaining the ~30,000-fold difference in Km between the intact receptor and synthetic peptides for phosphorylation by βAR kinase (Table III).

TABLE IV

Synthetic peptides of the hamster β2AR as inhibitors of $β_2AR$ phosphorylation by βAR kinase

| Peptide | $IC_{50}$ (μM) |
|---|---|
| NT (17–32) | ND |
| CI (56–74) | 40 |
| EI (97–106) | 300 |
| CII (137–151) | 240 |
| EII (177–190) | ND |
| CIII-1 (219–243) | 76 |
| CIII-2 (248–268) | 208 |
| CT-1 (337–355) | 320 |
| CT-2 (353–381) | 142 |
| CT-3 (396–418) | ND |

ND - no significant inhibition when tested at a concentration of ~500 μM.

Since the first intracellular loop $β_2AR$ peptide was the most potent inhibitor of $β_2AR$ phosphorylation by βAR kinase the specificity of this inhibition was studied further. As the length of the peptide decreases the ability to inhibit βAR kinase also decreases (Table V). In particular, shortening of the peptide from 15 to 11 amino acids results in a dramatic loss of the inhibition ($IC_{50}$ increases from 62 to 2600 μM). This indicates that one or more of the four amino acids removed (A,I,Y,F) is critical for the inhibition. Several mutant peptides with amino acid substitutions have also been synthesized. A peptide with Leu[64] and Asn[69] both changed to alanine does not appear to affect the inhibition. Converting Lys[60] and Arg[63] to alanine also does not significantly affect the inhibition. In contrast, a peptide which has Glu[62] changed to glutamine has significantly lower affinity as an inhibitor ($IC_{50}$ from 62 to 280 μM) suggesting that the glutamic acid is important in kinase interaction. Also shown in Table V are results from studies with peptides derived from the first intracellular loops of the β1-adrenergic receptor, the α2-adrenergic receptor and rhodopsin. It is evident that these peptides do not significantly inhibit $β_2AR$ phosphorylation by βAR kinase. Interestingly the $β_1AR$ peptide differs by only four amino acids (out of 15) from the $β_2AR$ peptide. However, one of these amino acids is Glu[62] which appears to be important for inhibition.

TABLE V

Comparison of first intracellular loop peptides as inhibitors of βAR kinase

| Peptide | Sequence | $IC_{50}$ (μM) |
|---|---|---|
| $β_2AR$ (56–74) | TAIAKFERLQTVTNYFITS | 40 |
| $β_2AR$ (57–71) | AIAKFERLQTVTNYF | 62 |
| $β_2AR$ (59–69) | AKFERLQTVTN | 1600 |
| $β_2AR$ (60–66) | KFERLQT | 2600 |
| $β_2AR$ (57–71, L→A, N→A) | AIAKFER<u>A</u>QTVT<u>A</u>YF | 43 |
| $β_2AR$ (57–71, K→A, R→A) | AIA<u>A</u>FE<u>A</u>LQTVTNYF | 88 |
| $β_2AR$ (57–71, E→Q) | AIAKF<u>Q</u>RLQTVTNYF | 280 |
| $β_1AR$ | AIAKTPRLQTLTNLF | 700 |
| $α_2AR$ | AVFTSRALKAPQNLF | >1000 |
| Rhodopsin | VTVQHKKLRTPLNYI | >1000 |

Further confirming the specificity of the peptide inhibition is the observation that the peptides failed to inhibit βAR kinase mediated phosphorylation of non-receptor substrates such as casein and phosvitin. Moreover, the first, second and third intracellular loop peptides did not inhibit βAR kinase phosphorylation of the carboxyl terminal βAR peptides.

For purposes of completing this disclosure, the entire contents of all publications cited hereinabove, are hereby incorporated by reference.

It will be clear to one skilled in the art to which the present invention relates from a reading of the above disclosure that certain changes in form and detail can be made without departing from the true scope of the invention.

What is claimed is:

1. A method of inhibiting desensitization of a cell to the effects of a compound, comprising causing the cell to be contacted with a pharmaceutically acceptable agent that inhibits β2 adrenergic receptor protein kinase and thereby inhibits β2 adrenergic receptor protein kinase-induced phosphorylation of β2 adrenergic receptors for said compound, which β2 adrenergic receptors are present on the surface of said cell, wherein said contacting is effected under conditions such that said inhibition of desensitization is effected.

2. The method according to claim 1 wherein said desensitization is homologous desensitization.

3. The method according to claim 1 wherein said compound is endogenous to said cell.

4. The method according to claim 1 wherein said compound is a drug.

5. The method according to claim 1 wherein said cell is a human cell.

6. The method according to claim 1 wherein said agent is a polyanion.

7. The method according to claim 1 wherein said agent is a peptide having the amino acid sequence of a fragment of a β2 adrenergic receptor present on the cell or a peptide having the β2 adrenergic receptor kinase inhibitory function thereof.

8. A method of inhibiting desensitization of a cell to the effects of a compound, comprising causing the cell to be contacted with a pharmaceutically acceptable agent that inhibits β2 adrenergic receptor protein kinase and thereby inhibits β2 adrenergic receptor protein kinase-induced phosphorylation of β2 adrenergic receptors for said compound, which β2 adrenergic receptors are present on the surface of said cell, wherein said contacting is effected under conditions such that said inhibition of desensitization is effected; and wherein said agent is a polyanion or a peptide derived from a β2 adrenergic receptor.

* * * * *